(12) United States Patent
Yamamoto

(10) Patent No.: US 6,855,525 B1
(45) Date of Patent: Feb. 15, 2005

(54) METHOD FOR PRODUCING OPTICALLY ACTIVE 4-HALO-3-HYDROXYBUTYRIC ACID ESTER

(75) Inventor: Hiroaki Yamamoto, Ibaraki (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/305,390

(22) Filed: May 5, 1999

(30) Foreign Application Priority Data

| May 8, 1998 | (JP) | 10-126507 |
| Oct. 21, 1998 | (JP) | 10-300178 |
| Apr. 5, 1999 | (JP) | 11-098205 |

(51) Int. Cl.$^7$ .............................. C12P 7/62; C07C 1/00
(52) U.S. Cl. ...................... 435/135; 435/189; 435/280; 435/183
(58) Field of Search ................ 435/135, 189, 435/280

(56) References Cited

U.S. PATENT DOCUMENTS

| 5,229,279 A | * | 7/1993 | Peoples et al. | 435/135 |
| 5,413,921 A | | 5/1995 | Onishi et al. | 435/135 |
| 5,559,030 A | * | 9/1996 | Matsuyama et al. | 435/280 |
| 6,001,618 A | * | 12/1999 | Kimoto et al. | 435/191 |
| 6,011,144 A | | 1/2000 | Steinbüchel et al. | 536/23.2 |

FOREIGN PATENT DOCUMENTS

| GB | 2132614 A | 7/1984 |
| WO | WO 93/02187 | 2/1993 |
| WO | WO 98/35025 | 8/1998 |

OTHER PUBLICATIONS

Kataoka, M. et al., "A Novel NADPH–Dependent Carbonyl Reductase of Candida macedoniensis: Purification and Characterization," Archives of Biochemistry and Biophysics, vol. 294, No. 2, pp. 469–474, 1992.

Nakamura, K. et al., Stereochemical Control of Microbial Reduction. 17. A Method for Controlling the Enantioselectivity of Reductions with Bakers' Yeast, J. Org. Chem., vol. 56, pp. 4778–4783, 1991.

Patel, Ramesh N. et al., Stereoselective reduction of β–keto esters by Geotrichum candidum, Enzyme Microb. Technol., vol. 14, pp. 731–738, 1992.

Shieh, Woan–Ru et al., "Stereochemical Control of Yeast Reductions. 5. Characterization of the Oxidoreductases Involved in the Reduction of β–Keto Esters," J. Am. Chem. Soc., vol. 107, pp. 2993–2994, 1985.

Peoples et al., "Poly–β–hydroxybutyrate Biosynthesis in Alcaligenes eutrophus H16," The Journal of Biological Chemistry, vol. 264, No. 26, pp. 15293–15297, 1989.

Rawlings et al., "The Gene Encoding *Escherichia coli* Acyl Carrier Protein Lies within a Cluster of Fatty Acid Biosynthetic Genes," The Journal of Biological Chemistry, vol. 267, pp. 5751–5754, 1992.

* cited by examiner

*Primary Examiner*—Richard Hutson
(74) *Attorney, Agent, or Firm*—Fish & Richardson P.C.

(57) ABSTRACT

The present invention provides a method for preparing (S)-4-halo-3-hydroxybutyric acid ester comprises asymmetric reduction of 4-halo-acetoacetic acid ester using β-ketoacyl-acylcarrier protein reductase constituting Type II fatty acid synthase or acetoacetyl-CoA reductase constituting the poly-β-hydroxy fatty acid synthesis system. β-ketoacyl-acyl carrier protein reductase constituting Type II fatty acid synthase or acetoacetyl-CoA reductase constituting the poly-β-hydroxy fatty acid synthesis system has a extremely high reducing activity as well as stereoseletivity for (S)-4-chloro-3-hydroxybutyric acid ester. In addition, the enzyme exhibits almost no oxidizing activity toward either configuration of ethyl 4-chloro-3-hydroxybutyrate, performing only the reducing reaction of ethyl, 4-chloroacetoacetate. Therefore, this enzyme can be used to efficiently produce (S)-4-halo-3-hydroxybutyric acid ester.

22 Claims, 4 Drawing Sheets

SEQUENCE LISTING

<160> NUMBER OF SEQ IDS NOS: 18

<210> SEQ ID NO 1
<211> LENGTH: 244
<212> TYPE: PRT
<213> ORGANISM: Escherichia coli

<400> SEQUENCE: 1

Met Asn Phe Glu Gly Lys Ile Ala Leu Val Thr Gly Ala Ser Arg Gly
1               5                   10                  15

Ile Gly Arg Ala Ile Ala Glu Thr Leu Ala Ala Arg Gly Ala Lys Val
            20                  25                  30

Ile Gly Thr Ala Thr Ser Glu Asn Gly Ala Gln Ala Ile Ser Asp Tyr
        35                  40                  45

Leu Gly Ala Asn Gly Lys Gly Leu Met Leu Asn Val Thr Asp Pro Ala
    50                  55                  60

Ser Ile Glu Ser Val Leu Glu Lys Ile Arg Ala Glu Phe Gly Glu Val
65                  70                  75                  80

Asp Ile Leu Val Asn Asn Ala Gly Ile Thr Arg Asp Asn Leu Leu Met
                85                  90                  95

Arg Met Lys Asp Glu Glu Trp Asn Asp Ile Ile Glu Thr Asn Leu Ser
            100                 105                 110

Ser Val Phe Arg Leu Ser Lys Ala Val Met Arg Ala Met Met Lys Lys
        115                 120                 125

Arg His Gly Arg Ile Ile Thr Ile Gly Ser Val Val Gly Thr Met Gly
    130                 135                 140

Asn Gly Gly Gln Ala Asn Tyr Ala Ala Ala Lys Ala Gly Leu Ile Gly
145                 150                 155                 160

Phe Ser Lys Ser Leu Ala Arg Glu Val Ala Ser Arg Gly Ile Thr Val
                165                 170                 175

Asn Val Val Ala Pro Gly Phe Ile Glu Thr Asp Met Thr Arg Ala Leu
            180                 185                 190

Ser Asp Asp Gln Arg Ala Gly Ile Leu Ala Gln Val Pro Ala Gly Arg
        195                 200                 205

Leu Gly Gly Ala Gln Glu Ile Ala Asn Ala Val Ala Phe Leu Ala Ser
    210                 215                 220

Asp Glu Ala Ala Tyr Ile Thr Gly Glu Thr Leu His Val Asn Gly Gly
225                 230                 235                 240

Met Tyr Met Val

<210> SEQ ID NO 2
<211> LENGTH: 735
<212> TYPE: DNA
<213> ORGANISM: Escherichia coli
<220> FEATURE:
<221> NAME/KEY: CDS
<222> LOCATION: (1)...(732)

<400> SEQUENCE: 2 atg aat ttt gaa gga aaa atc gca ctg gta acc ggt gca agc cgc gga     48
Met Asn Phe Glu Gly Lys Ile Ala Leu Val Thr Gly Ala Ser Arg Gly
1               5                   10                  15 att ggc cgc gca att gct gaa acg ctc gca gcc cgt ggc gcg aaa gtt     96
Ile Gly Arg Ala Ile Ala Glu Thr Leu Ala Ala Arg Gly Ala Lys Val
            20                  25                  30

```
att ggc act gcg acc agt gaa aat ggc gct cag gcg atc agt gat tat    144
Ile Gly Thr Ala Thr Ser Glu Asn Gly Ala Gln Ala Ile Ser Asp Tyr
        35                  40                  45 tta ggt gcc aac ggc aaa ggt ctg atg ttg aat gtg acc gac ccg gca    192
Leu Gly Ala Asn Gly Lys Gly Leu Met Leu Asn Val Thr Asp Pro Ala
 50                  55                  60 tct atc gaa tct gtt ctg gaa aaa att cgc gca gaa ttt ggt gaa gtg    240
Ser Ile Glu Ser Val Leu Glu Lys Ile Arg Ala Glu Phe Gly Glu Val
 65                  70                  75                  80 gat atc ctg gtc aat aat gcc ggt atc act cgt gat aac ctg tta atg    288
Asp Ile Leu Val Asn Asn Ala Gly Ile Thr Arg Asp Asn Leu Leu Met
                 85                  90                  95 cga atg aaa gat gaa gag tgg aac gat att atc gaa acc aac ctt tca    336
Arg Met Lys Asp Glu Glu Trp Asn Asp Ile Ile Glu Thr Asn Leu Ser
                100                 105                 110 tct gtt ttc cgt ctg tca aaa gcg gta atg cgc gct atg atg aaa aag    384
Ser Val Phe Arg Leu Ser Lys Ala Val Met Arg Ala Met Met Lys Lys
            115                 120                 125 cgt cat ggt cgt att atc act atc ggt tct gtg gtt ggt acc atg gga    432
Arg His Gly Arg Ile Ile Thr Ile Gly Ser Val Val Gly Thr Met Gly
130                 135                 140 aat ggc ggt cag gcc aac tac gct gcg gcg aaa gcg ggc ttg atc ggc    480
Asn Gly Gly Gln Ala Asn Tyr Ala Ala Ala Lys Ala Gly Leu Ile Gly
145                 150                 155                 160 ttc agt aaa tca ctg gcg cgc gaa gtt gcg tca cgc ggt att act gta    528
Phe Ser Lys Ser Leu Ala Arg Glu Val Ala Ser Arg Gly Ile Thr Val
                165                 170                 175 aac gtt gtt gct ccg ggc ttt att gaa acg gac atg aca cgt gcg ctg    576
Asn Val Val Ala Pro Gly Phe Ile Glu Thr Asp Met Thr Arg Ala Leu
            180                 185                 190 agc gat gac cag cgt gcg ggt atc ctg gcg cag gtt cct gcg ggt cgc    624
Ser Asp Asp Gln Arg Ala Gly Ile Leu Ala Gln Val Pro Ala Gly Arg
        195                 200                 205 ctc ggc ggc gca cag gaa atc gcc aac gcg gtt gca ttc ctg gca tcc    672
Leu Gly Gly Ala Gln Glu Ile Ala Asn Ala Val Ala Phe Leu Ala Ser
210                 215                 220 gac gaa gca gct tac atc acg ggt gaa act ttg cat gtg aac ggc ggg    720
Asp Glu Ala Ala Tyr Ile Thr Gly Glu Thr Leu His Val Asn Gly Gly
225                 230                 235                 240 atg tac atg gtc tga                                                735
Met Tyr Met Val <210> SEQ ID NO 3
<211> LENGTH: 36
<212> TYPE: DNA
<213> ORGANISM: Artificial Sequence
<220> FEATURE:
<223> OTHER INFORMATION: Artificially synthesized primer sequence

<400> SEQUENCE: 3
aaaggatcca acaatgaatt ttgaaggaaa aatcgc                             36

<210> SEQ ID NO 4
<211> LENGTH: 32
<212> TYPE: DNA
<213> ORGANISM: Artificial Sequence
<220> FEATURE:
<223> OTHER INFORMATION: Artificially synthesized primer sequence

<400> SEQUENCE: 4
tgcctcgagt tatcagacca tgtacatccc gc                                 32
```

```
<210> SEQ ID NO 5
<211> LENGTH: 248
<212> TYPE: PRT
<213> ORGANISM: Bacillus subtilis

<400> SEQUENCE: 5

Met Asp Met Leu Asn Asp Lys Thr Ala Ile Val Thr Gly Ala Ser Arg
  1               5                  10                  15

Gly Ile Gly Arg Ser Ile Ala Leu Ala Leu Ala Lys Ser Gly Ala Asn
             20                  25                  30

Val Val Val Asn Tyr Ser Gly Asn Glu Ala Lys Ala Asn Glu Val Val
         35                  40                  45

Asp Glu Ile Lys Ser Met Gly Arg Lys Ala Ile Ala Val Lys Ala Asp
 50                  55                  60

Val Ser Asn Pro Glu Asp Val Gln Asn Met Ile Lys Glu Thr Leu Ser
 65                  70                  75                  80

Val Phe Ser Thr Ile Asp Ile Leu Val Asn Asn Ala Gly Ile Thr Arg
             85                  90                  95

Asp Asn Leu Ile Met Arg Met Lys Glu Asp Glu Trp Asp Asp Val Ile
         100                 105                 110

Asn Ile Asn Leu Lys Gly Val Phe Asn Cys Thr Lys Ala Val Thr Arg
     115                 120                 125

Gln Met Met Lys Gln Arg Ser Gly Arg Ile Ile Asn Val Ser Ser Ile
130                 135                 140

Val Gly Val Ser Gly Asn Pro Gly Gln Ala Asn Tyr Val Ala Ala Lys
145                 150                 155                 160

Ala Gly Val Ile Gly Leu Thr Lys Ser Ser Ala Lys Glu Leu Ala Ser
             165                 170                 175

Arg Asn Ile Thr Val Asn Ala Ile Ala Pro Gly Phe Ile Ser Thr Asp
         180                 185                 190

Met Thr Asp Lys Leu Ala Lys Asp Val Gln Asp Glu Met Leu Lys Gln
     195                 200                 205

Ile Pro Leu Ala Arg Phe Gly Glu Pro Ser Asp Val Ser Ser Val Val
210                 215                 220

Thr Phe Leu Ala Ser Glu Gly Ala Arg Tyr Met Thr Gly Gln Thr Leu
225                 230                 235                 240

His Ile Asp Gly Gly Met Val Met
             245

<210> SEQ ID NO 6
<211> LENGTH: 747
<212> TYPE: DNA
<213> ORGANISM: Bacillus subtilis
<220> FEATURE:
<221> NAME/KEY: CDS
<222> LOCATION: (1)...(744)

<400> SEQUENCE: 6 atg gat atg ctt aat gat aaa acg gct att gtc act ggc gca tcc cgc      48
Met Asp Met Leu Asn Asp Lys Thr Ala Ile Val Thr Gly Ala Ser Arg
  1               5                  10                  15 gga atc ggc cgc tca atc gcc ctt gct ctg gca aaa agc gga gca aat      96
Gly Ile Gly Arg Ser Ile Ala Leu Ala Leu Ala Lys Ser Gly Ala Asn
             20                  25                  30 gtt gtc gtg aac tac tcc ggc aat gaa gcg aaa gca aat gaa gtg gta     144
Val Val Val Asn Tyr Ser Gly Asn Glu Ala Lys Ala Asn Glu Val Val
         35                  40                  45
```

```
gat gaa atc aaa tca atg ggc aga aaa gca att gct gta aaa gcg gat     192
Asp Glu Ile Lys Ser Met Gly Arg Lys Ala Ile Ala Val Lys Ala Asp
     50                  55                  60 gta tca aat ccc gaa gat gta caa aac atg ata aaa gaa aca ttg tct     240
Val Ser Asn Pro Glu Asp Val Gln Asn Met Ile Lys Glu Thr Leu Ser
 65                  70                  75                  80 gtt ttt tct acg att gac att ctg gtt aat aat gcg gga att aca aga     288
Val Phe Ser Thr Ile Asp Ile Leu Val Asn Asn Ala Gly Ile Thr Arg
                 85                  90                  95 gac aat ctc atc atg aga atg aaa gaa gac gaa tgg gat gac gtc att     336
Asp Asn Leu Ile Met Arg Met Lys Glu Asp Glu Trp Asp Asp Val Ile
                100                 105                 110 aac att aac ctg aag ggt gtt ttc aac tgc aca aaa gct gtt aca aga     384
Asn Ile Asn Leu Lys Gly Val Phe Asn Cys Thr Lys Ala Val Thr Arg
            115                 120                 125 caa atg atg aaa cag cgt tca ggc cgc att att aac gta tcg tct atc     432
Gln Met Met Lys Gln Arg Ser Gly Arg Ile Ile Asn Val Ser Ser Ile
        130                 135                 140 gtc ggc gtc agc gga aac cct gga caa gcc aac tac gtg gct gca aaa     480
Val Gly Val Ser Gly Asn Pro Gly Gln Ala Asn Tyr Val Ala Ala Lys
145                 150                 155                 160 gcc ggc gtc atc ggt tta acc aaa tct tct gct aaa gag ctc gcc agc     528
Ala Gly Val Ile Gly Leu Thr Lys Ser Ser Ala Lys Glu Leu Ala Ser
                165                 170                 175 cga aat att acg gta aac gca ata gcg cca gga ttt atc tca act gat     576
Arg Asn Ile Thr Val Asn Ala Ile Ala Pro Gly Phe Ile Ser Thr Asp
                180                 185                 190 atg aca gat aaa ctt gca aaa gac gtt caa gac gaa atg ctg aaa caa     624
Met Thr Asp Lys Leu Ala Lys Asp Val Gln Asp Glu Met Leu Lys Gln
            195                 200                 205 att ccg ctc gcg cgc ttt ggt gaa cct agc gat gtc agc agt gtt gtc     672
Ile Pro Leu Ala Arg Phe Gly Glu Pro Ser Asp Val Ser Ser Val Val
        210                 215                 220 acg ttc cta gct tca gag gga gct cgt tat atg aca ggc caa acg ctt     720
Thr Phe Leu Ala Ser Glu Gly Ala Arg Tyr Met Thr Gly Gln Thr Leu
225                 230                 235                 240 cat att gac ggc gga atg gtg atg taa                                 747
His Ile Asp Gly Gly Met Val Met
                245
```

<210> SEQ ID NO 7
<211> LENGTH: 33
<212> TYPE: DNA
<213> ORGANISM: Artificial Sequence
<220> FEATURE:
<223> OTHER INFORMATION: Artificially synthesized primer sequence

<400> SEQUENCE: 7
ggaccatgga tatgcttaat gataaaacgg cta     33

<210> SEQ ID NO 8
<211> LENGTH: 34
<212> TYPE: DNA
<213> ORGANISM: Artificial Sequence
<220> FEATURE:
<223> OTHER INFORMATION: Artificially synthesized primer sequence

<400> SEQUENCE: 8
gagaagcttc tcgagttaca tcaccattcc gccg     34

```
<210> SEQ ID NO 9
<211> LENGTH: 246
<212> TYPE: PRT
<213> ORGANISM: Ralstonia eutropha

<400> SEQUENCE: 9

Met Thr Gln Arg Ile Ala Tyr Val Thr Gly Gly Met Gly Gly Ile Gly
 1               5                  10                  15

Thr Ala Ile Cys Gln Arg Leu Ala Lys Asp Gly Phe Arg Val Val Ala
             20                  25                  30

Gly Cys Gly Pro Asn Ser Pro Arg Arg Glu Lys Trp Leu Glu Gln Gln
         35                  40                  45

Lys Ala Leu Gly Phe Asp Phe Ile Ala Ser Glu Gly Asn Val Ala Asp
 50                  55                  60

Trp Asp Ser Thr Lys Thr Ala Phe Asp Lys Val Lys Ser Glu Val Gly
 65                  70                  75                  80

Glu Val Asp Val Leu Ile Asn Asn Ala Gly Ile Thr Arg Asp Val Val
                 85                  90                  95

Phe Arg Lys Met Thr Arg Ala Asp Trp Asp Ala Val Ile Asp Thr Asn
            100                 105                 110

Leu Thr Ser Leu Phe Asn Val Thr Lys Gln Val Ile Asp Gly Met Ala
        115                 120                 125

Asp Arg Gly Trp Gly Arg Ile Val Asn Ile Ser Ser Val Asn Gly Gln
    130                 135                 140

Lys Gly Gln Phe Gly Gln Thr Asn Tyr Ser Thr Ala Lys Ala Gly Leu
145                 150                 155                 160

His Gly Phe Thr Met Ala Leu Ala Gln Glu Val Ala Thr Lys Gly Val
                165                 170                 175

Thr Val Asn Thr Val Ser Pro Gly Tyr Ile Ala Thr Asp Met Val Lys
            180                 185                 190

Ala Ile Arg Gln Asp Val Leu Asp Lys Ile Val Ala Thr Ile Pro Val
        195                 200                 205

Lys Arg Leu Gly Leu Pro Glu Glu Ile Ala Ser Ile Cys Ala Trp Leu
    210                 215                 220

Ser Ser Glu Glu Ser Gly Phe Ser Thr Gly Ala Asp Phe Ser Leu Asn
225                 230                 235                 240

Gly Gly Leu His Met Gly
                245

<210> SEQ ID NO 10
<211> LENGTH: 741
<212> TYPE: DNA
<213> ORGANISM: Ralstonia eutropha
<220> FEATURE:
<221> NAME/KEY: CDS
<222> LOCATION: (1)...(738)

<400> SEQUENCE: 10 atg act cag cgc att gcg tat gtg acc ggc ggc atg ggt ggt atc gga        48
Met Thr Gln Arg Ile Ala Tyr Val Thr Gly Gly Met Gly Gly Ile Gly
 1               5                  10                  15 acc gcc att tgc cag cgg ctg gcc aag gat ggc ttt cgt gtg gtg gcc        96
Thr Ala Ile Cys Gln Arg Leu Ala Lys Asp Gly Phe Arg Val Val Ala
             20                  25                  30 ggt tgc ggc ccc aac tcg ccg cgc cgc gaa aag tgg ctg gag cag cag       144
Gly Cys Gly Pro Asn Ser Pro Arg Arg Glu Lys Trp Leu Glu Gln Gln
         35                  40                  45
```

```
aag gcc ctg ggc ttc gat ttc att gcc tcg gaa ggc aat gtg gct gac      192
Lys Ala Leu Gly Phe Asp Phe Ile Ala Ser Glu Gly Asn Val Ala Asp
 50                  55                  60 tgg gac tcg acc aag acc gca ttc gac aag gtc aag tcc gag gtc ggc      240
Trp Asp Ser Thr Lys Thr Ala Phe Asp Lys Val Lys Ser Glu Val Gly
 65                  70                  75                  80 gag gtt gat gtg ctg atc aac aac gcc ggt atc acc cgc gac gtg gtg      288
Glu Val Asp Val Leu Ile Asn Asn Ala Gly Ile Thr Arg Asp Val Val
                 85                  90                  95 ttc cgc aag atg acc cgc gcc gac tgg gat gcg gtg atc gac acc aac      336
Phe Arg Lys Met Thr Arg Ala Asp Trp Asp Ala Val Ile Asp Thr Asn
            100                 105                 110 ctg acc tcg ctg ttc aac gtc acc aag cag gtg atc gac ggc atg gcc      384
Leu Thr Ser Leu Phe Asn Val Thr Lys Gln Val Ile Asp Gly Met Ala
        115                 120                 125 gac cgt ggc tgg ggc cgc atc gtc aac atc tcg tcg gtg aac ggg cag      432
Asp Arg Gly Trp Gly Arg Ile Val Asn Ile Ser Ser Val Asn Gly Gln
130                 135                 140 aag ggc cag ttc ggc cag acc aac tac tcc acc gcc aag gcc ggc ctg      480
Lys Gly Gln Phe Gly Gln Thr Asn Tyr Ser Thr Ala Lys Ala Gly Leu
145                 150                 155                 160 cat ggc ttc acc atg gca ctg gcg cag gaa gtg gcg acc aag ggc gtg      528
His Gly Phe Thr Met Ala Leu Ala Gln Glu Val Ala Thr Lys Gly Val
                165                 170                 175 acc gtc aac acg gtc tct ccg ggc tat atc gcc acc gac atg gtc aag      576
Thr Val Asn Thr Val Ser Pro Gly Tyr Ile Ala Thr Asp Met Val Lys
            180                 185                 190 gcg atc cgc cag gac gtg ctc gac aag atc gtc gcg acg atc ccg gtc      624
Ala Ile Arg Gln Asp Val Leu Asp Lys Ile Val Ala Thr Ile Pro Val
        195                 200                 205 aag cgc ctg ggc ctg ccg gaa gag atc gcc tcg atc tgc gcc tgg ttg      672
Lys Arg Leu Gly Leu Pro Glu Glu Ile Ala Ser Ile Cys Ala Trp Leu
210                 215                 220 tcg tcg gag gag tcc ggt ttc tcg acc ggc gcc gac ttc tcg ctc aac      720
Ser Ser Glu Glu Ser Gly Phe Ser Thr Gly Ala Asp Phe Ser Leu Asn
225                 230                 235                 240 ggc ggc ctg cat atg ggc taa                                          741
Gly Gly Leu His Met Gly
                245
```

<210> SEQ ID NO 11
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 11
agtggatcca atgactcagc gcattgcgta                                     30

<210> SEQ ID NO 12
<211> LENGTH: 35
<212> TYPE: DNA
<213> ORGANISM: Artificial Sequence
<220> FEATURE:
<223> OTHER INFORMATION: Artificially synthesized primer sequence

<400> SEQUENCE: 12
aacaagcttc tcgagttagc ccatatgcag gccgc                               35

```
<210> SEQ ID NO 13
<211> LENGTH: 31
<212> TYPE: DNA
<213> ORGANISM: Artificial Sequence
<220> FEATURE:
<223> OTHER INFORMATION: Artificially synthesized  sequence

<400> SEQUENCE: 13
aattctcgag taatctagag gaattctaaa a                              31

<210> SEQ ID NO 14
<211> LENGTH: 31
<212> TYPE: DNA
<213> ORGANISM: Artificial Sequence
<220> FEATURE:
<223> OTHER INFORMATION: Artificially synthesized sequence

<400> SEQUENCE: 14
ctagttttag aattcctcta gattactcga g                              31

<210> SEQ ID NO 15
<211> LENGTH: 35
<212> TYPE: DNA
<213> ORGANISM: Artificial Sequence
<220> FEATURE:
<223> OTHER INFORMATION: Artificially synthesized primer sequence

<400> SEQUENCE: 15
gaggaattca tacatgtatc cagatttaaa aggaa                          35

<210> SEQ ID NO 16
<211> LENGTH: 30
<212> TYPE: DNA
<213> ORGANISM: Artificial Sequence
<220> FEATURE:
<223> OTHER INFORMATION: Artificially synthesized primer sequence

<400> SEQUENCE: 16
ggtaagcttt cattaaccgc ggcctgcctg                                30

<210> SEQ ID NO 17
<211> LENGTH: 806
<212> TYPE: DNA
<213> ORGANISM: Bacillus subtilis
<220> FEATURE:
<221> NAME/KEY: CDS
<222> LOCATION: (12)...(794)

<400> SEQUENCE: 17
ggaattcata c atg tat cca gat tta aaa gga aaa gtc gtc gct att aca     50
            Met Tyr Pro Asp Leu Lys Gly Lys Val Val Ala Ile Thr
              1               5                  10 gga gct gct tca ggg ctc gga aag gcg atg gcc att cgc ttc ggc aag      98
Gly Ala Ala Ser Gly Leu Gly Lys Ala Met Ala Ile Arg Phe Gly Lys
     15                  20                  25 gag cag gca aaa gtg gtt atc aac tat tat agt aat aaa caa gat ccg     146
Glu Gln Ala Lys Val Val Ile Asn Tyr Tyr Ser Asn Lys Gln Asp Pro
 30                  35                  40                  45 aac gag gta aaa gaa gag gtc atc aag gcg ggc ggt gaa gct gtt gtc     194
Asn Glu Val Lys Glu Glu Val Ile Lys Ala Gly Gly Glu Ala Val Val
                 50                  55                  60 gtc caa gga gat gtc acg aaa gag gaa gat gta aaa aat atc gtg caa     242
Val Gln Gly Asp Val Thr Lys Glu Glu Asp Val Lys Asn Ile Val Gln
             65                  70                  75
```

-continued

```
acg gca att aag gag ttc ggc aca ctc gat att atg att aat aat gcc     290
Thr Ala Ile Lys Glu Phe Gly Thr Leu Asp Ile Met Ile Asn Asn Ala
         80                  85                  90 ggt ctt gaa aat cct gtg cca tct cac gaa atg ccg ctc aag gat tgg     338
Gly Leu Glu Asn Pro Val Pro Ser His Glu Met Pro Leu Lys Asp Trp
     95                 100                 105 gat aaa gtc atc ggc acg aac tta acg ggt gcc ttt tta gga agc cgt     386
Asp Lys Val Ile Gly Thr Asn Leu Thr Gly Ala Phe Leu Gly Ser Arg
110                 115                 120                 125 gaa gcg att aaa tat ttc gta gaa aac gat atc aag gga aat gtc att     434
Glu Ala Ile Lys Tyr Phe Val Glu Asn Asp Ile Lys Gly Asn Val Ile
                130                 135                 140 aac atg tcc agt gtg cac gaa gtg att cct tgg ccg tta ttt gtc cac     482
Asn Met Ser Ser Val His Glu Val Ile Pro Trp Pro Leu Phe Val His
                145                 150                 155 tat gcg gca agt aaa ggc ggg ata aag ctg atg aca gaa aca tta gcg     530
Tyr Ala Ala Ser Lys Gly Gly Ile Lys Leu Met Thr Glu Thr Leu Ala
                160                 165                 170 ttg gaa tac gcg ccg aag ggc att cgc gtc aat aat att ggg cca ggt     578
Leu Glu Tyr Ala Pro Lys Gly Ile Arg Val Asn Asn Ile Gly Pro Gly
        175                 180                 185 gcg atc aac acg cca atc aat gct gaa aaa ttc gct gac cct aaa cag     626
Ala Ile Asn Thr Pro Ile Asn Ala Glu Lys Phe Ala Asp Pro Lys Gln
190                 195                 200                 205 aaa gct gat gta gaa agc atg att cca atg gga tat atc ggc gaa ccg     674
Lys Ala Asp Val Glu Ser Met Ile Pro Met Gly Tyr Ile Gly Glu Pro
                210                 215                 220 gag gag atc gcc gca gta gca gcc tgg ctt gct tcg aag gaa gcc agc     722
Glu Glu Ile Ala Ala Val Ala Ala Trp Leu Ala Ser Lys Glu Ala Ser
                225                 230                 235 tac gtc aca ggc atc acg tta ttc gcg gac ggc ggt atg aca caa tat     770
Tyr Val Thr Gly Ile Thr Leu Phe Ala Asp Gly Gly Met Thr Gln Tyr
            240                 245                 250 cct tca ttc cag gca ggc cgc ggt taatgaaagc tt                       806
Pro Ser Phe Gln Ala Gly Arg Gly
        255                 260
```

<210> SEQ ID NO 18
<211> LENGTH: 261
<212> TYPE: PRT
<213> ORGANISM: Bacillus subtilis

<400> SEQUENCE: 18

```
Met Tyr Pro Asp Leu Lys Gly Lys Val Val Ala Ile Thr Gly Ala Ala
  1               5                  10                  15

Ser Gly Leu Gly Lys Ala Met Ala Ile Arg Phe Gly Lys Glu Gln Ala
             20                  25                  30

Lys Val Val Ile Asn Tyr Tyr Ser Asn Lys Gln Asp Pro Asn Glu Val
         35                  40                  45

Lys Glu Glu Val Ile Lys Ala Gly Gly Glu Ala Val Val Val Gln Gly
     50                  55                  60

Asp Val Thr Lys Glu Glu Asp Val Lys Asn Ile Val Gln Thr Ala Ile
 65                  70                  75                  80

Lys Glu Phe Gly Thr Leu Asp Ile Met Ile Asn Asn Ala Gly Leu Glu
                 85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125
```

-continued

```
Lys Tyr Phe Val Glu Asn Asp Ile Lys Gly Asn Val Ile Asn Met Ser
    130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
            180                 185                 190

Thr Pro Ile Asn Ala Glu Lys Phe Ala Asp Pro Lys Gln Lys Ala Asp
        195                 200                 205

Val Glu Ser Met Ile Pro Met Gly Tyr Ile Gly Glu Pro Glu Glu Ile
    210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260
```

METHOD FOR PRODUCING OPTICALLY ACTIVE 4-HALO-3-HYDROXYBUTYRIC ACID ESTER

FIELD OF THE INVENTION

The present invention relates to a method for preparing (S)-4-halo-3-hydroxybutyric acid ester using β-ketoacyl-acylcarrier-protein reductase comprising Type II fatty acid synthase or acetoacetyl-CoA reductase comprising poly-β-hydroxy fatty acid. synthase.

BACKGROUND OF THE INVENTION

Known methods for preparing the optically active (S)-4-halo-3-hydroxybutyric acid ester include an asymmetric reduction method using 3-α-hydroxysteroid dehydrogenase (Japanese Patent Laid-Open Publication No. Hei 1-277494) and microorganisms such as baker's yeast (J. Am. Chem. Soc. 105, 5925–5926 (1983); Japanese Patent Laid-Open Publication No. Sho 61-146191). D-enzyme-1 and D-enzyme-2 have been reported as the enzyme of baker's yeast reducing 4-haloacetoacetic acid ester to produce (S)-4-halo-3-hydroxybutyric acid ester (J. Org. Chem. 56, 4778–4483 (1991)). Of these enzymes, D-enzyme-2 has been indicated to be the fatty acid synthase based on its molecular weight, etc. (J. Am. Chem. Soc. 107, 2993 (1985)).

However, in the synthesis of optically active (S)-4-halo-3-hydroxybutyric acid ester by reducing 4-haloacetoacetic acid ester using baker's yeast, the enzymatic activity is too low to produce the desired product in a high concentration. Furthermore, since baker's yeast has an enzyme reducing 4-haloacetoacetic acid ester to produce (R)-4-halo-3-hydroxybutyric acid ester, it is difficult to stably synthesize (S)-4-halo-3-hydroxybutyric acid ester with a high optical purity.

In addition, the fatty acid synthase mainly involved in the synthesis of (S)-4-halo-3-hydroxybutyric acid ester in baker's yeast has been reported to be quickly inhibited by SH reagents such as iodoacetamide, mercury, and p-(chloromercury)benzoic acid. Thus, the enzyme is expected to be inhibited by the substrate 4-haloacetoacetic acid ester and the product 4-halo-3-hydroxybutyric acid ester. Therefore, baker's yeast is not preferable for producing (S)-4-halo-3-hydroxybutyric acid ester in a large quantity.

It is also conceivable to synthesize (S)-4-halo-3-hydroxybutyric acid ester with a high optical purity by highly expressing the fatty acid synthase of baker's yeast with a high specific activity in heterologous microorganisms using genetic engineering techniques. However, the fatty acid synthase of baker's yeast is an extremely complex multicatalytic enzyme, in which α-subunit with the molecular weight of 208,000 consisting of 1,894 amino acid residues and β-subunit with the molecular weight of 229,000 consisting of 2,051 amino acid residues (J. Biol. Chem. 263, 12315–12325 (1988)) form an α6β6 complex (J. Biol. Chem. 253, 4464–4475 (1978)), having eight different activities, besides the β-keto group reducing activity (β-ketoacyl-ACP reducing activity), including the acyl carrier protein (ACP) activity, ACP-S-acetyltransferase activity, ACP-S-malonyl transferase activity, β-ketoacyl-ACP synthase activity, β-hydroxyacyl-ACP dehydrogenase activity, enoyl-ACP reductase activity, and palmitoyl transferase activity. Therefore, it is not easy to highly express this synthase in heterologous microorganisms. For example, an attempt to express FAS1 and FAS2 in minicells of *E. coli* reportedly resulted in failure to detect a full length of the enzymes (Ann. Rev. Biochem. 52, 537–579 (1983)).

The domain for the β-ketoacyl-ACP reducing activity which is expected to exhibit the 4-haloacetoacetic acid ester reductase activity has been indicated to be located in the α-subunit of the fatty acid synthase based on the amino acid sequence. It has been reported, however, that, when the α-subunit was completely dissociated by freeze-thawing in a high salt concentration (Biochem. J. 109, 312–314 (1968)) and by lysine modification with dimethyl maleic anhydride, the subunit alone did not express the β-ketoacyl-ACP reducing activity (Eur. J. Biochem. 94, 189–197 (1979)). It has also been reported that ethyl acetoacetate reducing activity was not expressed by the fatty acid synthase with an α6β6 structure but expressed only by that with an α2β2 structure (Mw 800,000) (Eur. J. Biochem. 172, 633–639 (1988)). Therefore, it has not been clarified which domain of the fatty acid synthase is essential for the 4-haloacetoacetic acid reducing activity and how to efficiently prepare the structure (α2β2) expressing the 4-haloacetoacetic acid ester reducing activity.

SUMMARY OF THE INVENTION

An objective of the present invention is to provide a method for efficiently producing (S)-4-halo-3-hydroxybutyric acid ester utilizing an enzyme constituting fatty acid synthase or that constituting the poly-β-hydroxy fatty acid biosynthetic system.

Fatty acid synthase is structurally classified into four types, IA, IB, IC, and II (Shin Seikagaku Jikken Koza (New Biochemical Experiment) 4, Shisitu (Lipids) I, p34–37). Animals including humans (Proc. Natl. Acad. Sci. USA 92, 8695 (1995)) have Type IA synthase comprising a homodimer (Mw about 500,000) of α-subunit (Mw about 250,000) having all of the above-described eight different activities of fatty acid synthase. Yeasts including baker's yeast and fungi have Type IB synthase of an α6β6 structure (Mw about 2,400,000) consisting of α-subunit (Mw about 210,000) and A-subunit (Mw about 200,000) expressing all the fatty acid synthase activities. Bacteria such as *Brevibacterium ammoniagenes* (Eur. J. Biochem. 247, 268 (1997)) and *Micobacterium smegmatis* (Physiol. Rev. 56, 339 (1976)) have Type IC synthase of an α6 structure consisting of α-subunit (Mw about 250,000) having all the fatty acid synthase activities. Plants such as *Brassica napus* (Biochim. Biophys. Acta, 1120, 151 (1992)) and algae, bacteria such as *Esherichia coli, Actinomycetes*, and viruses have Type II synthase in which individual reactions of the fatty acid synthase are carried out with separate enzyme proteins.

Taking notice of β-ketoacyl-ACP reductase classified into Type II fatty acid synthase, among these various types of enzymes, which is simpler in the structure and functions, smaller in molecular weight (Mw of subunit about 20,000 to 40,000) as compared with Type I enzymes (IA, IB, and IC), and not inhibited by SH reagents, the present inventors have thought that, if the enzyme has the activity to reduce 4-haloaetoaetic acid ester to synthesize (S)-4-halo-3-hydroxybutyric acid ester like Type IB fatty acid synthase of baker's yeast, it would be possible to produce (S)-4-halo-3-hydroxybutyric acid ester in a large quantity and create a microbial strain capable of producing (S)-4-halo-3-hydroxybutyric acid ester in high yield utilizing genetic engineering techniques.

Therefore, the present inventors have attempted the isolation of β-ketoacyl-ACP reductase constituting Type II fatty acid synthase to investigate its reducing activity toward 4-haloaetoaetic acid ester. Specifically, β-ketoacyl-ACP reductase genes of *Escherichia coli* or *Bacillus subtilis*, whose nucleotide sequences were known, were cloned by the polymerase chain reaction with chromosomal DNAs from respective bacteria as the template. The isolated gene was then introduced into *Escherichia coli* to highly express the enzyme therein to examine its 4-chloroacetoaetic acid ester reducing activity. As a result, the present inventors have found that the enzyme has an extremely high reducing activity and steroselectivity toward 4-chloroacetoacetic acid ester.

In addition, while it has been reported that β-ketoacyl-ACP reductase from *Escherichia coil* showed an oxidizing activity specific to the D-stereoisomer of β-hydroxybutyl-ACP (J. Biol. Chem. 240, 618–621 (1965)), the present inventors have found that the enzyme as well as the enzyme derived from *Bacillus subtilis* showed almost no oxidizing activity to 4-chloro-3-hydroxybutyric acid ester of either configuration, but only reducing ethyl 4-chloroacetoacetate. Such a property is extremely advantageous for synthesizing an optically active (S)-4-halo-3-hydroxybutyric acid ester by asymmetric reduction because the reaction equilibrium is not rate-limiting.

Furthermore, the present inventors have found that genes encoding acetoacetyl-CoA reductase (generally designated phbB or phaB), one of the enzymes constituting the poly-β-hydroxy fatty acid (PHA) biosynthesis system, have homology to that encoding Type II fatty acid synthase (generally designated fabG), and examined whether these acetoacetyl-CoA reductases are capable of asymmetrically reducing 4-chloroacetoacetic acid ester to (S)-4-halo-3-hydroxybutyric acid ester like β-ketoacyl-ACP reductase. Specifically, the inventors isolated the acetoacetyl-CoA reductase gene from *Ralstonia eutropha*, introduced the resulting gene to *Escherihia coli* to express it, and used the expressed acetoacetyl-CoA reductase to reduce 4-chloroacetoacetic acid ester. As a result, it has been found that the enzyme has a high reducing activity and stereoselectivity for producing (S)-4-chloro-3-hydroxybutyric acid ester.

The inventors also have found that acetoacetyl-CoA reductase, like β-ketoacyl-ACP reductase, shows almost no reactivity to either optical isomer of 4-chloro-3-hydroxybutyric acid ester, and practically functions as only the reductase, which is favorable to the synthesis of (S)-4-chloro-3-hydroxybutyric acid ester.

Furthermore, the present inventors have attempted to efficiently accelerate the reducing reaction cycle by regenerating the coenzyme (NADPH or NADH), which is consumed associated with the asymmetric reduction of 4-chloroacetoacetic acid ester in this reducing reaction system. First, the inventors introduced into *Escherihia coli* a gene encoding glucose dehydrogenase capable of regenerating the coenzyme (NADPH or NADH) and a gene encoding β-ketoacyl-ACP reductase, thereby obtaining *E. coli* strain capable of producing these enzymes. Then, ethyl 4-haloacetoacetate was reduced utilizing the thus-obtained transformant to measure the yield and the optical purity of ethyl (S)-chloro-3-hydroxybutyrate thus produced. As a result, it was found that the recombinant enzyme produced by the *Escherihia coli* strain has a high enzymatic activity quite suitable for producing ethyl (S)-chloro-3-hydroxybutyrate with a high optical purity.

The present invention relates to a method for producing (S)-4-halo-3-hydroxybutyric acid ester by reacting 4-halo-acetoacetic acid ester or its derivatives with β-ketoacyl-ACP reductase constituting Type II fatty acid synthase or acetoacetyl-CoA reductase, one of the enzymes constituting the poly-β-hydroxy fatty acid biosynthesis system. More specifically, it relates to:

(1) a method for producing (S)-4-halo-3-hydroxybutyric acid ester comprising asymmetrically reducing 4-haloacetoacetic acid ester or its derivatives with β-ketoacyl-acyl carrier protein reductase constituting Type II fatty acid synthase, (2) the method of (1), wherein said β-ketoacyl carrier protein reductase is derived from *Escherihia coli*, (3) the method of (1), wherein said β-ketoacyl carrier protein reductase is selected from the group consisting of:
  (a) a protein comprising the amino acid sequence of SEQ ID NO: 1;
  (b) a protein comprising a modified amino acid sequence of SEQ ID NO: 1 in which one or more amino acid residues are added, deleted, or substituted and capable of asymmetrically reducing 4-haloacetoacetic acid ester or its derivatives to produce (S)-4-halo-3-hydroxybutyric acid ester; and
  (c) a protein encoded by DNA hybridizable with the DNA comprising the nucleotide sequence of SEQ ID NO: 2 and capable of asymmetrically reducing 4-haloacetoacetic acid ester or its derivatives to produce (S)-4-halo-3-hydroxybutyric acid ester, (4) the method of (1), wherein said β-ketoacyl-acyl carrier protein reductase is derived from microorganisms belonging to the genus *Bacillus*, (5) the method of (4), wherein said β-ketoacyl-acyl carrier protein reductase is derived from *Bacillus subtilis*, (6) the method of (1), wherein said β-ketoacyl-acyl carrier protein reductase is selected from the group consisting of:
  (a) a protein comprising the amino acid sequence of SEQ ID NO: 5;
  (b) a protein comprising a modified amino acid sequence of SEQ ID NO: 5 in which one or more amino acid residues are added, deleted, or substituted and capable of asymmetrically reducing 4-haloacetoacetic acid ester or its derivatives to produce (S)-4-halo-3-hydroxybutyric acid ester; and
  (c) a protein encoded by DNA hybridizable with the DNA comprising the nucleotide sequence of SEQ ID NO: 6 and capable of asymmetrically reducing 4-haloacetoacetic acid ester or its derivatives to produce (S)-4-halo-3-hydroxybutyric acid ester, (7) a method for producing (S)-4-halo-3-hydroxybutyric acid ester comprising asymmetrically reducing 4-haloacetoacetic acid ester or its derivatives with acetoacetyl-CoA reductase constituting the poly-β-hydroxy fatty acid biosynthesis system, (8) a method of (7), wherein said acetoacetyl-CoA reductase is derived from microorganisms belonging to the genus *Ralstonia*, (9) a method of (8), wherein said acetoacetyl-CoA reductase is derived from *Ralstonia eutropha*,

(10) the method of (7), wherein said acetoacetyl-CoA reductase is selected from the group consisting of:
  (a) a protein comprising the amino acid sequence of SEQ ID NO: 9;
  (b) a protein comprising a modified amino acid sequence of SEQ ID NO: 9 in which one or more amino acid residues are added, deleted, or substituted and capable of asymmetrically reducing 4-haloacetoacetic acid ester or its derivatives to produce (S)-4-halo-3-hydroxybutyric acid ester; and (c) a protein encoded by DNA hybridizable with the DNA comprising the nucleotide sequence of SEQ ID NO: 10 and capable of asymmetrically reducing 4-haloacetoacetic acid ester or its derivatives to produce (S)-4-halo-3-hydroxybutyric acid ester,

(11) the method of (1) or (7), wherein said 4-haloacetoacetic acid ester is 4-chloroacetoacetic acid ester,

(12) the method of (1) or (7), wherein said 4-haloacetoacetic acid ester is ethyl 4-chloroacetoacetate,

(13) the method of (1), wherein said method uses a microorganism capable of producing β-ketoacyl-acyl carrier protein reductase constituting Type II fatty acid synthase and an enzyme catalyzing production of NAD(P)H from NAD(P)$^+$,

(14) the method of (13), wherein said microorganism is a recombinant microorganism into which heterologous or homologous DNA encoding the β-ketoacyl-acyl carrier protein reductase constituting Type II fatty acid synthase and heterologous or homologous DNA encoding an enzyme catalyzing production of NAD(P)H from NAD(P)$^+$, and is capable of expressing both enzymes,

(15) the method of (14), wherein said microorganism is Escherihia coli,

(16) the method of any one of (13) through (15), wherein said enzyme catalyzing production of NAD(P)H from NAD(P)$^+$ is glucose dehydrogenase,

(17) the method of (7), wherein said method uses a microorganism capable of producing acetoacetyl-CoA reductase constituting the poly-β-hydroxy fatty acid biosynthesis system and an enzyme catalyzing production of NAD(P)H from NAD(P)$^+$,

(18) the method of (17), wherein said microorganism is a recombinant microorganism into which heterologous or homologous DNA encoding acetoacetyl-CoA reductase constituting the poly-β-hydroxy fatty acid biosynthesis system and heterologous or homologous DNA encoding an enzyme catalyzing production of NAD(P)H from NAD(P)$^+$ and capable of expressing both enzymes,

(19) the method of (18), wherein said microorganism is Escherichia coli, and

(20) the method of any one of (17) through (19), wherein said enzyme catalyzing production of NAD(P)H from NAD(P)$^+$ is glucose dehydrogenase.

DETAILED DESCRIPTION OF THE INVENTION

Figure 1:
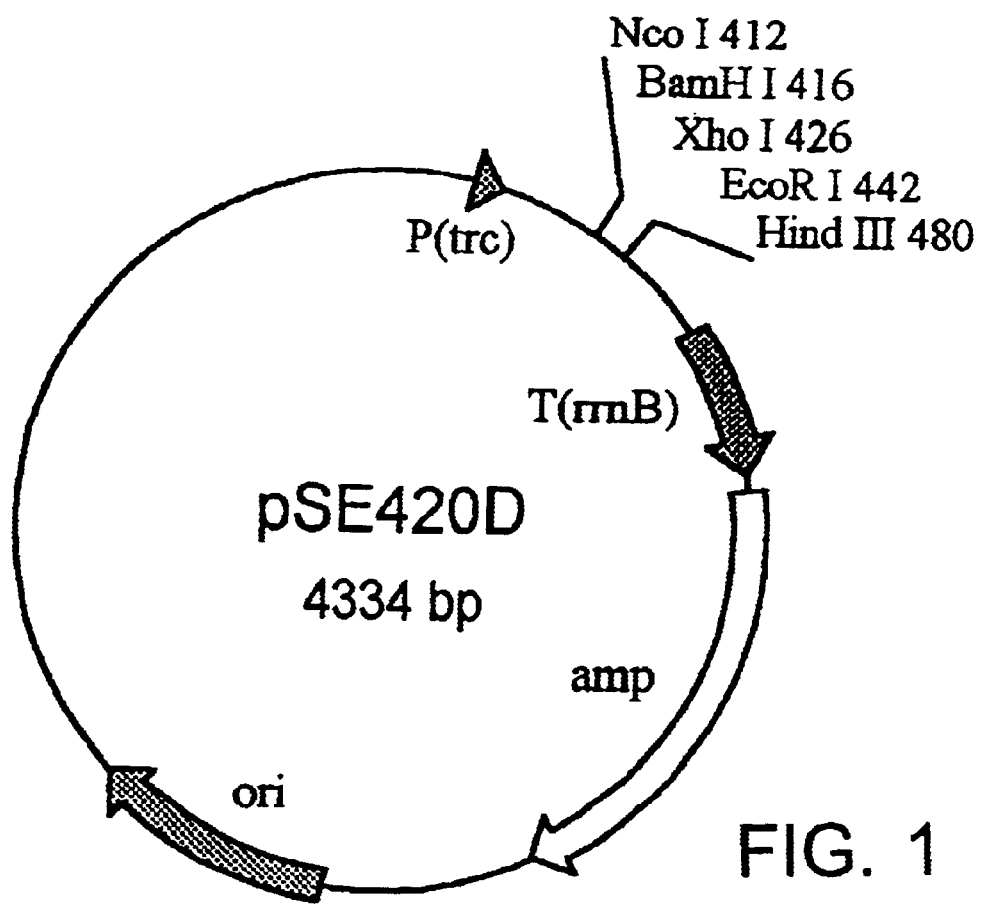
FIG. 1 shows the restriction map of plasmid pSE420D. P(trc) represents the trc promoter, T(rrnB) the rrnB T1T2 terminator, Amp the β-lactamase gene for ampicillin resistance, and ori the replication origin of plasmid.

The method for producing (S)-4-halo-3-hydroxybutyric acid ester of the present invention uses the enzyme constituting Type II fatty acid synthase (EC1.1.1.100) or acetoacetyl-CoA reductase (EC 1.1.1.36) constituting the PHA biosynthesis system. The enzyme (EC 1.1.1.100) constituting Type II fatty acid synthase is simpler in the structure and functions, smaller in the molecular weight (Mw of subunit about 20,000 to 40,000), and no inhibited by SH reagents as compared with Type IA synthase comprising a homodimer of α-subunit, Type IB synthase of an α6β6 structure consisting of α-subunit and β-subunit, and Type IC synthase of an α6 structure of α-subunit, which have all of various activities of fatty acid synthase. Therefore, Type II synthaseiis advantageous and preferable for large quantity production of (S)-4-halo-3-hydroxybutyric acid ester and construction of a microbial strain capable of high level producion of (S)-4-halo-3-hydroxybutyric acid ester.

The source of the synthase used is not particularly limited. In addition to β-ketoacyl-ACP reductase derived from Escherichia coli (:SEQ ID NO: 1, J. Biol. Chem. 267, 5751–5754 (1992)) and that derived from Bacillus subtilis (SEQ ID NO: 5, J. Bacteriol. 178, 4794–4800 (1996)), and enzymes derived from other various organisms can be used. The enzymes derived from other organisms include β-ketoacyl-ACP reductase derived from Actinobacillus actinomycetemcomitans (Biochem. Biophys. Res. Commun, 230, 220–225 (1997)), Bacillus subtilis (J. Bacteriol. 178, 4794–4800 (1996)), Escherichia coli (J. Biol. Chem. 267, 5751–5754 (1992)), Mycobacterium bovis (Science 267, 227–230 (1994)), Mycobacterium smegmatis (DDBJ Accession number U66800), Mycobacterium tuberculosis (Mol. Microbiol. 15, 1009–1015 (1995)), Propionibacterium shermanii (J. Gen. Microbiol. 127, 121–129 (1981)), Streptococcus pneumoniae (WO97/43303), Synechocystis sp. (DNARes. 3, 109–136 (1996)), Thermotoga maritima (J. Bacteriol. 178, 248–257 (1996)), Vibrio harveyi (J. Bacteriol. 178, 571–573 (1996)), Haemophilus influenza (Science 269, 469–512 (1995)), etc. β-ketoacyl-ACP reductases derived from plants include those derived from Allium porrum (Plant Physiol. 115, 501–510 (1997)), Arabidopsis thaliana (Biochem. J. 283, 321–326 (1992), Plant Physiol. 115, 501–510 (1997)), Brassica napus (WO96/02652)), Carthamus tinctorius (Arch. Biochem. Biophys. 217, 144–154 (1982)), Cuphea lanceolata (Mol. Gen. Genet. 233, 122–128 (1992)), Hordeum vulgare (Plant Physiol. 115, 501–510 (1997)), Persea americana (Biochem. J. 271, 713–720 (1990)), carrot (Arch. Biochem. Biophys. 300, 157–163 (1993)), Euglena gracilis (J. Biol. Chem. 255, 1504–1508 (1980)), Spinacia oleracea (Plant Physiol. 69, 1257–1262 (1982)), Zea mays L. (Plant Physiol. 115, 501–510 (1997)), etc.

A gene encoding β-ketoacyl-ACP reductase can be isolated utilizing, for example, hybridization techniques. A β-ketoacyl-ACP reductase gene derived from various organisms can be isolated by hybridization, under the stringent conditions, with the DNA encoding β-ketoacyl-ACP reductase derived from Escherichia coli (SEQ ID NO: 2) and that from Bacillus subtilis (SEQ ID NO: 6), or DNAs prepared from other organisms using the portions thereof as the probe. The polymerase chain reaction can also be utilized to isolate the desired gene. For example, primers are designed based on the highly homologous region in the gene encoding β-ketoacyl-ACP reductase (e.g. NADPH-binding region, 10th to 34th amino acid residues of β-ketoacyl-ACP reductase from *Escherichia coli*) and, using the resulting primers and the chromosomal DNA or CDNA of a target organism as the template, the polymerase chain reaction is performed to isolate the gene encoding β-ketoacyl-ACP reductase from various organisms.

Poly-β-hydroxy fatty acid (PHA) is known to accumulate in more than 100 varieties of prokaryotic microorganisms including the genus *Alcaligenes, Aphanothece, Azotobacter, Bacillus, Pseudomonas, Rhodospirillum*, and *Actinomyces*. The PHA biosynthetic system comprises 3-ketothiolase, acetoacetyl CoA reductase and PHA synthase. Among them, acetoacetyl CoA reductase comprises a tetramer of the subunit with Mw 20,000 to 40,000 and preferably uses reduced nicotinamide adenine dinuleotide phosphate (NADPH) as the coenzyme for the reducing reaction. It can also employ a more economical and highly stable reduced nicotinamide adenine dinucleotide (NADH) as the coenzyme and thus is industrially advantageous.

Any acetoacetyl CoA reductases can be used in the present invention regardless of their origin so far as they are acetoacetyl CoA reductase participating in the PHA biosynthesis. Examples thereof include acetoacetyl CoA reductase derived from *Acinetobacter* sp. RA3849 (J. Bacteriol. 177, 4501–4507 (1995)), *Ralstonia eutropha* (previously called *Alcaligenes eutrophus*, FEMS Microbiol. Lett. 52, 259–264 (1988)), *Alcaligenes latus* (J. Microbiol. Biotechnol. 6, 425–431 (1996)), *Alcaligenes* sp. SH-69 (DDBJ Accession No. AF002014), *Azospirillum brasilense* (J. Gen. Microbiol. 136, 1191–1196 (1990), Mol. Gen. Genet. 231, 375–384 (1992)), *Azotobater beijerinckii* (Biochem. J., 134, 225–238 (1973)), *Bacillus megaterium* (Can. J. Microbiol. 41 (Suppl. 1), 77–79 (1995)), *Chromatium vinosum* D strain (Eur. J. Biochem. 209, 135–150 (1992)), *Ectothiorhodospira shaposhnikovii* (Appl. Microbiol. Biotechnol. 40, 292–300 (1993)), *Lupinus luteus* (Plant Soil, 56, 379–390 (1980)), *Methylobacterium extorquens* (FEMS Microbiol. Lett. 156, 275–279 (1997)), *Methylobacterium rhodesianum* MB 126 (Arch. Microbiol. 161, 277–280 (1994)), *Paracoccus denitricans* (FEMS Microbiol. Rev. 103, 257–264 (1992), FEMS Microbiol. Lett. 133, 85–90 (1995)), *Pseudomonas* sp. (DDBJ Accession No. Z80156), *Rhizobium lupini* (Fiziol. Rast. (Moscow) 27, 544–550 (1980)), *Rhizobium meliloti* 41 or *Sinorhizobium meliloti* (Microbiology, 141, 2553–2559 (1995)), *Rhodococus ruber* NCIMB 40126 (FEMS Microbiol. Rev., 103, 93–101 (1992)), *Synechococcus* sp. (Japanese Patent Laid-open Publication No. Hei 6-187085), *Syntrophomonas wolfei* subsp. *wolfei* (Arch. Microbiol. 159, 16–20 (1993)), *Thiocapsa pfennigii* (Appl. Microbiol. Biotechnol. 40, 292–300 (1993)), and *Zoogloea ramigera* I-16-M (Arch. Microbiol. 114, 211–217 (1977), J. Biol. Chem. 262, 97–102 (1987)).

If the nucleotide sequence of the gene encoding acetoacetyl-CoA reductase is known, the coding region can be isolated using the polymerase chain reaction (PCR). The acetoacetyl-CoA reductase gene can also be isolated from various organisms by hybridizing, under the stringent conditions, the target DNA with DNA encoding acetoacetyl-CoA reductase derived from, for example, *Ralstonia eutropha* (SEQ ID NO: 10, the amino acid sequence of the enzyme is shown in SEQ ID NO: 9) or DNA prepared from other organisms using the portions of the above enzyme-encoding DNA as the probe. Furthermore, it is also possible to isolate the acetoacetyl-CoA reductase gene from various organisms utilizing the polymerase chain reation (PCR) with primers designed based on a highly homologous region (such as the NADPH-binding region) of the gene encoding acetoacetyl-CoA reductase and the chromosomal DNA or CDNA from a target organism as the template.

In the method of the present invention, may be used not only naturally-occurring enzymes but also variant enzymes having modified amino acid sequence of the natural enzyme so far as the variant enzymes are functionally equivalent to the natural enzyme. Such modification of the amino acid sequence can be made by the method using BAL31 exonulease III, Kunkel method, and PCR, which are well known to those skilled in the art (Labomanual Genetic Engineering, 3rd ed., p219–230, Maruzen). Since the amino acid substitution may occur spontaneously, not only enzymes having amino acid artificially modified but also enzymes with spontaneously modified amino acid sequence can be used in the present invention.

In addition, the enzyme genes used in the method of the present invention include the gene having homology to β-ketoacyl-ACP reductase or acetoacetyl-CoA reductase and encoding Type II synthase of polyketides biosynthesized through the system similar to that of fatty acid synthesis and PHB synthesis (e.g. the open reading frame (ORF)-3 gene of the actI gene derived from *Sachropolyspora hirsuta*, Mol. Gen. Genet. 240, 146–150 (1993)), ORF-5 in the gene having homology to the above actI gene derived from *Streptomyces cinnamonensis* and putatively participating in the biosynthesis of monensin (Mol. Gen. Genet. 234, 254–264 (1992)), actIII that is a gene for actinorhodin biosynthesis derived from *Streptomyces coelicolor* (Gene 74, 305–320 (1988)), aknA that is a gene for Aklavinone biosynthesis derived from *Streptomyces galilaeus* (J. Bacteriol., 176, 2473–2475 (1994)), dauB that is a gene for daunomyin biosynthesis derived from *Streptomyces* sp. C5 (J. Bacteriol., 176, 6270–6280 (1994)), ORF-5 of the gene for granaticin polyketide synthase putative ketoacyl reductase 1 derived from *Streptomyces violaceoruber* Tu22, ORF-6 of the gene for the granaticin polyketide synthase putative ketoacyl reductase 2 (EMBO J., 8, 2717–2725 (1989), etc.), nodG that is a gene involved in the nodulation derived from *Rhizobium meliloti* RCR2011 (Nucleic Acids Res. 14, 7453–7472 (1986)), and hetN that is a gene involved in the heterocyst formation derived from *Anabaena* sp. (PCC 7120) (J. Bacteriol. 176, 2282–2292 (1994)). These can be preferably used as long as enzymes (such as β-ketoacyl reductase), products of these genes, have the activity to reduce 4-halo-acetoacetic acid ester to produce (S)-4-halo-3-hydroxybutyric acid.

In the present invention, "asymmetric reduction of 4-halo-acetoacetic acid ester or its derivatives using β-ketoacyl-acyl carrier protein (ACP) reductase or acetoacetyl-CoA reductase" is not necessarily perfomed using the purified enzyme. Microorganisms and plants containing said enzyme, or thier treated products can also,be used. Especially, it is preferable to use organisms transformed with a heterologous or homologous gene encoding β-ketoacyl-ACP reductase or acetoacetyl-CoA reductase using genetic engineering techniques to enable high level expression of the enzyme or the treated products, of the organisms. If the organism having β-ketoacyl-ACP reductase or acetoacetyl-CoA reductase also possesses the enzyme reducing 4-halo-acetoacetic acid ester or its derivatives to synthesize (R)-4-halo-3-hydroxybutyric acid ester, such a organism is preferably mutated to delete these (R)-enatiomer generating enzymes by the natural or artificial mutation or recombinant DNA techniques.

The host microorganisms used the present invention are not particularly limitated as long as they can be transformed with DNA encoding the polypeptide having the activity of β-ketoacyl-ACP reductase or acetoacetyl-CoA reductase and express these enzyme activities. Specific examples thereof include bacteria for which the host vector system has been developed, such as the genera *Escherichia, Bacillus, Pseudomonas, Serratia, Brevibacterium, Corynebacterium, Streptococcus,* and *Lactobacillus,* yeasts such as *Saccharomyces, Kluyveromyces, Schizosaccharomyces, Zygosaccharomyces, Yarrowia, Trichosporon, Rhodosporidium, Hansenula, Pichia,* and *Candida,* and fungi such as the genera *Neurospora, Aspergillus, Cephalosporium,* and *Trichoderma.*

Transformants can be prepared by techniques conventionally used in the field of molecular biology, biotechnology, and genetic engineering (e.g., Sambrook et al., Molocular Cloning, Cold Spring Harbor Laboratories). In order to express the gene for β-ketoacyl-ACP reductase or acetoacetyl-CoA reductase of the present invention in miroorganisms and the like host, it is necessary to first introduce the gene into a plasmid or phage vector that can be stably present in miroorganisms to transcript and translate the genetic information. For that purpose, as the unit for controlling the transcription and translation, a promoter can be incorporated upstream of the 5'-side of the gene and a terminator downstream of the 3'-side of the gene. Any promoter and terminator can be used so far as they function in microorganisms to be used as the host. Vetors, promoters, and terminaters functioning in various microorganisms are described in detail in "Biseibutugaku Kisokoza (Fundamental Microbiology), 8, Idenshikogaku (Genetic Engineering), Kyoritsu", especially those usable in yeast in Adv. Biochem. Eng. 43, 78–102 (1980) and Yeast 8, 423–488 (1992).

For example, in the genus *Escherichia,* especially in *Esherichia coli,* pBR and pUC series can be used as the plasmid vector. Examples of the promoters include those derived from lac (β-galactosidase), trp (tryptophan operon), tac (lac and trp fused), phage λ PL, and PR. The terminators include trpA terminator and rrnB ribosomal terminator.

In the genus *Bacillus,* the plasmid pUB110 pC194 series can be used as the vector. These vectors can be integrated into chromosomes. as the promoter and the terminator, those for apr (alkaline protease), npr (neutral protease), and amy (.-amylase) can be used.

In the genus *Pseudomonas,* the host-vector system has been developed in *Pseudomonas putida, Pseudomonas cepacia,* etc. Vectors with a broad host spetrum such as pKT240 (comprising the gene required for the autonomous replication derived from RSF1010 or the like) developed based on the plasmid TOL participating in the degradation of toluene compounds can be used. An example of the promoter and terminator that can be used is those for the lipase gene (Japanese Patent Laid-Open Publication No. Hei 5-284973).

In the genus *Brevibacterium,* especially in *Brevibacterium lactofermentum,* the plsamid vector such as pAJ43 (Gene 39, 281 (1985)) can be used. In this vector, the promoters and terminators employed in *Escherichia coli* can be used.

In the genus *Corynebacterium,* especially in *Corynebacterium glutamicum,* the plasmid vectors such as pCS11 (Japanese Patent Laid-Open Publication No. Sho 57-183799) and pCB101 (Mol. Gen. Genet. 196, 175 (1984)) can be used.

In the genus *Streptococcus,* pHV1301 (FEMS Microbiol. Lett. 26, 239 (1985)) and pGK1 (Appl. Environ. Microbiol. 50, 94 (1985)) can be used as the plasmid vector.

In the genus *Lactobacillus,* vector pAMβ1 (J. Bacteriol. 137, 614 (1979)) developed for the genus *Streptococcus* and the promoter used in *Escherichia coli* can be employed.

In the genus *Saccharomyces,* especially in *Saccharomyces cerevisiae,* the plasmid YRp series, YEp series, YCp series, and YIp series can be used. The integration vector that utilizes the homologous recombination with the ribosomal RNA present in multicopies in A chromosome (EP 537456) is extremely useful because it allows to integrate muticopies of a gene and stably maintain them. The promoters and terminators that can be used in this yeast are those for ADH (alcohol dehydrogenase), GAPDH (glyceraldehyde-3-phosphate dehydrogenase), PHO (acidic phosphatase), GAL (β-galactosidase), PGK (phosphoglycerate kinase), and ENO (enolase).

In the genus *Kluyveromyces,* especially in *Kluyveromyces lactis,* examples of the vectots include the plasmid 2 μm series derived from *Saccharomyces cerevisiae,* pKD1 series (J. Bacteriol. 145, 382–390 (1981)), plasmids derived from pKG11 concerned with the killer activity, KARS series which is the autonomous replication gene in the genus *Kluyveromyces,* and the vector plasmid capable of integrating to chromosome by the homologous recombination with ribosomal RNA (EP 537456). Promoters and terminators derived from ADH, PGK, etc. can be used.

In the genus *Schizosaccharomyces,* the vectors to be used are ARS (the autonomous replication-related gene) derived from *Schizosaccharomyces pombe* and the plasmid vector containing the selection marker complementing the autotrophy derived from *Saccharomyces cerevisiae* (Mol. Cell Biol. 6, 80 (1986)). ADH promoter derived from *Schizosaccharomyces pombe* can be used (EMBO J. 6, 729 (1987)).

In the genus *Zygosaccharomyces,* the plasmid vector based on pSB3 (Nucleic Aids Res. 13, 4267 (1985)) derived from *Zygosaccharomyces rouxii* can be used. Examples of the promoters are PHO5 promoter derived from *Saccharomyces cerevisiae,* GAP-Zr (glyceraldehyde-3-phosphate dehydrogenase) promoter derived from *Zygosaccharomyces rouxii* (Agri. Biol. Chem. 54, 2521 (1990)).

In the genus *Hansenula,* the host vector has been developed in *Hansenula polymorpha*. The autonomous replication-related genes HARS1 and HARS2 derived from *Hansenula polymorpha* can be used as the vector. Since they are relatively unstable, the multicopy integration to chromosome is effective (Yeast 7, 431–443 (1991)). AOX promoter (alcohol oxidase) induced by methanol and FDH (formate dehydrogenase) promoter can be used.

In the genus *Pichia,* the host-vector system has been developed in *Pichia pastoris* utilizing the genes (PARS1 and PARS2) involved in the autonomous replication for *Pichia* (Mol. Cell. Biol. 5, 3376 (1985)). In this vector, the potent promoter such as AOX inuducible by the high concentration culture and methanol can be used (Nucleic Acids Res. 15, 3859 (1987)).

In the genus *Candida,* the host-vector system has been developed in *Candida maltosa, Candida albicans, Candida tropicalis, Candida utilis, Candida boidinii,* etc (Japanese Patent Laid-Open Publication No. Hei 5-344895). *Candida maltosa*-derived ARS has been cloned (Agri. Biol. Chem. 51, 1587 (1987)) and used to develop a vector. In *Candida utilis,* a potent promoter has been developed for the vector capable of chromosomal integration (Japanese Patent Laid-Open Publication No. Hei 8-173170).

In the genus *Aspergillus, Aspergillus niger, Aspergillus oryzae,* etc. have been most comprehensively studied among funji. Plasmids derived from these species and vectors capable of chromosomal integration are available. Promoters for the extracellular proteases and amylases can be used (Trends in Biotehnology 7, 283–287 (1989)).

In the genus *Trichoderma*, the *Trichoderma reesei*-based host-vector system has been developed. In this vector the promoter for the extracellular cellulase gene can be used (Biotechnology 7, 596–603 (1989)).

The culturing of transformants and purification of recombinant proteins from transformants can be performed by the conventional method known to those skilled in the art.

The substrate for the enzyme in the present invention is 4-halo-acetoacetic acid ester or its derivatives such as those with a substituent at the α-position. Preferable substrates are 4-chloroacetoacetic acid ester and ethyl 4-chloroacetoacete. The substrate concentration used in the method of this invention ranges usually from 0.1 to 50%, preferably from 1 to 20%. The enzyme amount used ranges usually from 0.01 to 500 U/ml of the reaction mixture, preferably from 0.1 to 50 U/ml. The coenzyme (NADPH or NADH) required by the enzyme is added in the reaction system if necessary in an amount of 0.00001 to 5 equivalents, preferably 0.0001 to 1 equivalent, with respect to the amount of the substrate. A buffer solution (for example, a phosphate buffer) can be used as a solvent in the reaction system to maintain the pH. A aqueous two-phase reaction system containing 10 to 90% organic solvent such as octane, hexane, toluene, ethyl acetate, n-butyl acetate, and chloroform can also be used. The reaction temperture is usually 4 to 50° C., preferably 10 to 30° C. pH is adjusted to usually 3 to 9, preferably 4 to 8. The reaction product, (S)-4-halo-3-hydroxybutyric acid ester, can be extracted by an organic solvent capable of dissolving the product well such as ethyl acetate and octane and purified by a method such as distillation.

In the above-described reaction, $NADP^+$ produced from NADPH during the reducing reaction is suitably converted to NADPH (acetoacetyl-CoA reductase and β-ketoacyl reductase involved in the biosynthesis of PHA and polyketides utilize not only NADPH but also NADH). The regeneration of the coenzymes can be performed utilizing the $NAD(P)^+$ reducing ability (such as the glycolytic pathway) of miroorganisms. The $NAD(P)^+$ reducing ability can be increased by supplementing the reaction system with glucose or ethanol or by adding a microorganism capable of generating NAD(P)H from $NAD(P)^+$, treated products thereof, or the enzyme with such an activity. For example, NAD(P)H can be regenerated using microorganisms having glucose dehyrogenase, malate dehydrogenase, glutamate dehydrogenase, formate dehydrogenase, alcohol dehydrogenase, amino acid dehydrogenase, and/or glycerol dehydrogenase, treated products thereof, or the purified enzymes. Furthermore, the microorganism capable of producing β-ketoacyl reductase or acetoacetyl-CoA reductase can be genetically engineered to highly express these enzymes with the NAD(P)H regenerating activity, and the resulting transformant or the treated product thereof can be used in the method of the present invention.

In the present invention, it is also possible to use microorgansims capable of producing both acetoacetyl-CoA reductase and the NAD(P)H regenerating enzyme or both β-ketoacyl reductase and the NAD(P)H regenerating enzyme, or the treated products thereof. Such microorganisms can further genetically engineered to highly express these enzymes and the resulting microorganisms or their treated products can be used in the method of the present invention.

In the method of producing (S)-4-halo-3-hydroxybutyric acid ester using the microorganism capable of producing both acetoacetyl-CoA reductase and the NAD(P)H regenerating enzyme or both β-ketoacyl reductase and the NAD (P)H regenerating enzyme, or the treated products thereof, 1/50 to 1/20 volume, preferably 1/10 to 1/5 volume, based on the reaction mixture, of the culture, microbial cells recovered from the culture, or treated products thereof can be used. $NAD^+$ or $NADP^+$ can be added to the reaction mixture if necessary in an amount of 0.00001 to 5 equivalents, preferably 0.0001 to 1 equivalent, with respect to the amount of the substrate.

The reaction can also be performed using a bioreactor in which the microorganism producing the two enzymes or treated products thereof is immobilized on κ-carrageenan, acrylamide, polyurethane, chitin, or the like carrier. The reaction using the bioreactor can be performed by continuously supplying 4-halo-acetoacetic acid ester as the substrate, the substrate for regenerating the coenzyme (e.g. glucose when glucose dehydrogenase is used as the enzyme for regenerating the coenzyme), and if required, a buffer for controlling pH, and $NAD^+$ or $NADP^+$ as the coenzyme, or repeatedly using the reaction mixture.

The present invention provides a method of producing the optically active (S)-4-halo-3-hydroxybutyric acid ester using β-ketoacyl-acyl carrier protein reductase constituting Type II fatty acid synthase or acetoacetyl-CoA reductase constituting the poly-β-hydroxy fatty acid biosynthesizing system. β-Ketoacyl-acyl carrier protein reductase constituting Type II fatty acid synthase is especially advantageous for constructing a highly productive system using genetic recombination techniques, enabling a more efficient production of the optically active (S)-4-halo-3-hydroxybutyric acid ester as compared with the prior art techniques.

The present invention will be described in more detail with reference to examples, but is not construed to be limited to these examples.

EXAMPLE 1

Isolation of β-Ketoacyl-ACP Reductase Gene from *Escherichia coli*

*Escherichia coli* JM109 strain was cultured in the LB medium (containing Bacto-Tryptone 10 g, Bacto-Yeast extract 5 g, and NaCl 10 g/l) and the chromosomal DNA was prepared from the bacteria thus obtained using a Qiagen Genomic-tip (Qiagen). For the PCR cloning of the β-ketoacyl-ACP reductase gene (fabG) (J. Biol. Chem. 267, 5751–5754 (1992)) of *Escherichia coli*, the primers ECR-ATG1 (5'-AAAGGATCCAACAATGAATTTTGAAGG-AAAAATCGC-3', SEQ ID NO: 3) and ECR-TAG1 (5'-TGCCTCGAGTTATCAGACCATGTACATCCCGC-3', SEQ ID NO: 4) were synthesized based on the nucleotide sequences at the 5'- and 3'-ends of the structural gene. Using the chromosomal DNA of *Escherichia coli* as the template, and the ECR-ATG1 and ECR-TAG1 primers, 30 cycles of PCR (95° C. for 30 sec, 50° C. for 1 min, and 75° C. for 2 min) were performed to obtain the amplified DNA fragments.

The resulting DNA fragments were digested with restriction enzymes BamHI and XhoI. The plasmid vector pSE420 (Invitrogen) was g digested with NcoI and BamHI, treated with the Klenow fragment, and subjeted to the self-cyclyzation reation to obtain the plasmid pSE420B. This pSE420B was digested with BamHI and XhoI, and ligated to the above PCR amplified fragments digested with the same two restriction enzymes using T4 DNA ligase to obtain the plasmid pSE-ECRI. The DNA insert in the plasmid thus obtained were sequenced and identified as the fabG gene. The nucleotide sequence of fabg is shown in SEQ ID NO: 2 and the amino acid sequence of the protein encoded by the gene in SEQ ID NO: 1.

EXAMPLE 2

Expression of β-Ketoacyl-ACP Reductase Gene from *Escherichia coli*

*Escherichia coli* HB101 strain was transformed with pSE-ECR1 and the resulting transformant (*E. coli* HB101 (pSE-ECR1)) was cultured in the LB medium (5 ml) containing ampicillin (50 mg/ml) overnight. IPTG was added to the medium to 0.1 mM and the culture was further incubated for 5 h. Bacterial cells thus obtained were collected, disrupted with a Minibeatbeater 8 (BIOSPEC), and centrifuged to obtain the supernatant as the cell-free extract.

EXAMPLE 3

Reducing Activity of β-Ketoacyl-ACP Reductase from *Escherichia coli*

The reducing activity of the cell-free extract obtained in Example 2 was assayed using ethyl 4-chloroacetoacetate, ethyl acetoacetate, and acetoacetyl-CoA as the substrate.

A reaction mixture containing 50 mM potassium phosphate buffer (pH 6.5), 0.2 mM NADPH, and 20 mM the substrate (0.2 mM when acetoacetyl-CoA was used as the substrate) and the enzyme was allowed to react at 25° C. One unit of the enzyme was defined as the amount of the enzyme catalyzing the decrease of 1 μmol of NADPH for 1 min. The results are shown in Table 1. In this table, ECAA represents ethyl 4-chloroacetoacetate, EAA ethyl acetoacetate, and AASCoA acetoacetyl-CoA, R the reducing activity, and DH the dehydrogenase activity.

TABLE 1

|  | NADPH-ECAA-R | NADPH-AASCoA-R | NADPH-EAA-R | NADP+-R-ECHB-DH | NADP+-S-ECHB-DH |
|---|---|---|---|---|---|
| Cell-free extract | 100% | 116% | 1.90% | 0.010% | 0.004% |

The cell-free extract expressing β-ketoacyl-ACP reductase showed the NADPH-dependent ethyl 4-chloroacetoacetate-reducing activity, and its specific activity was 0.90 U/mg protein. In contrast, the HB101 strain containing no plasmid pSE-ECR1 showed almost no ethyl 4-chloroacetoacetate-reducing activity. The extract showed approximately the same activity for acetoacetyl-CoA as that for ethyl 4-chloroacetoacetate, while almost no activity for ethyl acetoacetate having no chlorine group.

EXAMPLE 4

Oxidizing Activity of β-Ketoacyl-ACP Reductase Derived from *Escherichia coli*

The oxdizing activity of the cell-free extract obtained in Example 2 was assayed using ethyl (S)- or (R)-4-chloro-3-hydroxybutyrate as the substrate. The oxdizing reaction was performed by incubating a reaction mixture containing 50 mM Tris-HCl buffer (pH 9.0), 2.5 mM NADP+, 20 mM the substrate, and the enzyme at 25° C. One unit of enzyme was defined as the amount of enzyme catalyzing the increase of 1 μmol of NADPH for min. The results are shown in Table 1. As shown in Table 1, the extract showed almost no oxidizing activity for either substrate. In this table, ECHB represents ethyl 4-chloro-3-hydroxybutyrate.

EXAMPLE 5

Stereoseletivity of β-Ketoacyl-ACP Reductase Derived from *Escherichia coli* for Ethyl 4-chloro-3-hydoxybutyrate A reaction mixture (1 ml) containing 200 mM potassium phosphate buffer (pH 6.5), 146 mM NADPH, 2% ethyl 4-chloroacetoacetate (122 mM), and β-ketoacyl-ACP reductase (2 U) prepared in Example 2 was incubated at 20° C. overnight. Aliquot of the reaction solution was diluted 2-fold with 0.1 N HCl and ethyl 4-chloro-3-hydroxybutyrate contained in the diultion was determined by gas chromatography. Gas chromatography was performed with a Thermon 3000 chromosolve W (2 m, Shinwakako) under the conditions of the column temperature of 150° C. and the detection temperature of 250° C. using a flame ionization detector (FID). As a result, the concentration of ethyl 4-chloro-3-hydroxybutyrate was found to be 13.3 g/l with a yield of 66.3%.

Optical purity was assayed by extracting ethyl 4-chloro-3-hydroxybutyrate from the reaction mixture with ethyl acetate, removing the solvent, and subjecting the residue to the high-performance liquid chromatography using an optical resolution column (column, chiracel OD (Daicel Chemical)); mobile phase, n-hexane/isopropanol (9/2); RI detection; flow rate, 0.5 ml/min). As a result, the optical purity was 96.5% ee (S) or more.

EXAMPLE 6

Synthesis of Ethyl 4-chloro-3-hydoxybutyrate by β-Ketoacyl-ACP Reductase Derived from *Escherichia coli*

A reaction solution (1 ml) containing 200 mM potassium phosphate buffer solution (pH 6.5), 2% ethyl 4-chloroacetoacetate (122 mM), 1.0 mM NADPH, β-ketoacyl-ACP reductase (1 U), 250 mM glucose, and glucose dehydrogenase (Wako Pure Chemical) (10 U) was incubated at 25° C. for 16 h. Analysis was performed in the same manenr as in Example 5, idicating that ethyl 4-chloro-3-hydoxybutyrate with the optical purity of 95.4% ee (S) or more was synthesized in a yield of 98.4%.

EXAMPLE 7

Isolation of β-Ketoacyl-ACP Reductase Gene from *Bacillus subtilis*

*Bacillus subtilis* BGSC 1A1 strain was cultured in the LB medium (containing Bacto-Tryptone 10 g, Bacto-Yeast extract 5 g, and NaCl 10 g/l), and the chromosomal DNA was prepared from the microbial cells thus obtained using a Qiagen Genomic-tip (Qiagen). For the PCR cloning of the β-ketoacyl-ACP reductase gene (fabG) of *Bacillus subtilis*, the primers BSR-ATG1 (5'-GGACCATGGATATGCTTAATGATAAAACGGCTA-3', SEQ ID NO: 7) and BSR-TAA1 (5'-GAGAAGCTTCTCGAGTTACATCACCATTCCGCCG-3', SEQ ID NO: 8) were synthesized based on the sequences at the 5'- and 3'-ends of the structural gene. Using the chromosomal DNA of *Bacillus subtilis* as the template and the BSR-ATG1 and BSR-TAA1 primers, 30 cycles of PCR (95° C. for 30 sec, 50° C. for 1 min, and 75° C. for 2 min) were performed to obtain the amplified DNA fragments.

The DNA fragments thus obtained were digested with NcoI and HindIII. The plasmid vector pSE420 (Invitrogen) was digested with NcoI and HindIII, and linked to the above PCR-amplified fragments digested with the same two restriction enzymes using T4 DNA ligase to obtain the plasmid pSE-BSR1. The DNA inserts in the plasmid thus obtained were sequenced, identifying them to be the fabG gene except for one amino acid substitution. Namely, GCT corresponding to Ala at the position 25 according to the database (DDBJ (DNA Data Bank of Japan, Accession No. U59433) was replaced by GAT encoding Asp at the position 25. The nucleotide sequence of the fabG gene thus obtained is shown in SEQ ID NO: 6, the amino acid sequence of the protein encoded by the gene in SEQ ID NO: 5.

EXAMPLE 8

Expression of β-Ketoacyl-ACP Reductase Gene derived from *Bacillus subtilis*

*Escherichia coli* HB101 strain was transformed with pSE-BSR1 and the resulting transformant (*E. coli* HB101 (pSE-BSR1)) was cultured in the LB medium (7 ml) containing ampicillin (50 mg/ml) overnight. IPTG was added to the medium to 0.1 mM and the culture was further incubated for 5 h. Bacterial cells thus obtained were collected, disrupted with a Minibeatbeater 8 (BIOSPEC), and centrifuged to obtain the supernatant as the cell-free extract.

EXAMPLE 9

Reducing Activity of β-Ketoacyl-ACP Reductase Derived from *Bacillus subtilis*

The reducing activity of the cell-free extract obtained in Example 8 was assayed using ethyl 4-chloroacetoacetate and acetoacetyl-CoA as the substrate in the same manner as in Example 3.

The results are shown in Table 2. In this table, ECAA represents ethyl 4-chloroacetoacetate and AASCoA acetoacetyl-CoA.

TABLE 2

| Substrate | ECAA | | AASCoA | S-ECHB | R-ECHB |
|---|---|---|---|---|---|
| Coenzyme | NADPH | NADH | NADPH | NADP+ | NADP+ |
| U/mg | 0.133 | 0 | 0.030 | 0.002 | 0.002 |
| Relative activity | 100% | 0.0% | 22.3% | 1.3% | 1.3% |

The cell-free extract expressing β-ketoacyl-ACP reductase showed the NADPH-dependent ethyl 4-chloroacetoacetate-reduce activity and its specific activity was 0.133 U/mg protein. In contrast, the HB101 strain containing no plasmid pSE-BSR1 showed almost no ethyl 4-chloroacetoacetate-reducing activity. The acetoacetyl-CoA-reducing activity was as low as about 22% of ethyl 4-chloroacetoacetate-reducing activity, revealing the difference from the enzyme derived from *Escherichia coli*.

EXAMPLE 10

Oxidizing Activity of β-Ketoacyl-ACP Reductase Derived from *Bacillus subtilis*

The oxdizing activity of the cell-free extract obtained in Example 8 was assayed using ethyl (S)- or (R)-4-chloro-3-hydroxybutyrate as the substrate in the same manner as in Example 4. The results are shown in Table 2. The cell extract showed almost no activity for either substrate. In table 2, ECHB represents ethyl 4-chloro-3-hydroxybutyrate.

EXAMPLE 11

Stereoselectivity of β-Ketoacyl-ACP Reductase Derived from *Bacillus subtilis*

A reaction mixture (1 ml) containing 200 mM potassium phosphate buffer (pH 6.5), 1 mM NADP+, 2% ethyl 4-chloroacetoacetate (122 mM), β-ketoacyl-ACP reductase (0.8 U) prepared in Example 8, 250 mM glucose, and glucose dehyrogenase (3.2 U) (Wako Pure Chemical) was incubated at 25° C. for one day. Analysis was performed by the method according to Example 5, indicating that ethyl 4-chloro-3-hydroxybutyrate was quantitatively synthesized with the optical purity of 98.1% ee (S) or more.

EXAMPLE 12

Isolation of Acetoacetyl-CoA Reductase Gene from *Ralstonia eutropha*

*Ralstonia eutropha* DSM 531 was cultured in a bouillon medium (containing beaf extracts 5.0 g, peptone 15.0 g, NaCl 5.0 g, and K$_2$HPO$_4$ 5.0 g/l) and the chromosomal DNA was prepared from the microbial cells thus obtained using a Qiagen Genomic-tip (Qiagen).

For the PCR cloning of the acetoacetyl-CoA reductase gene (phbB) of *Ralstonia eutropha*, the primers AER-ATG1 (5'-AGTGGATCCAATGACTCAGCGCATTGCGTA-3', SEQ ID NO: 11) and AER-TAA1 (5'-AACAAGCTTCTCGAGTTAGCCCATATGCAGGCCGC-3', SEQ ID NO: 12) were synthesized based on the sequences at the 5'- and 31-ends of the structural gene.

Using the chromosomal DNA of *Ralstonia eutropha* as the template and the AER-ATG1 and AER-TAA1 primers, 30 cycles of PCR (95° C. for 30 sec, 50° C. for 1 min and 75° C. for 2 min) were performed to obtain the amplified DNA fragments.

The thus-obtained DNA fragments were digested with BamHI and HindIII. The plasmid vector pSE420 prepared by the method of Example 1 was digested with BamHI and HindIII and the digestion product was ligated to the above PCR-amplified fragments digested with the same two restriction enzymes using T4 DNA ligase to obtain the plasmid pSE-AER1.

The DNA insert in the plasmid thus obtained were sequenced and identified as the phbb gene.

EXAMPLE 13

Expression of Acetoacetyl-CoA Reductase Gene Derived from *Ralstonia eutropha*

*Escherichia coli* HB101 strain was transformed with pSE-AER1 and the resulting transformant (*E. coli* HB101 (pSE-AER1)) was cultured in the LB medium (7 ml) containing ampicillin (50 mg/ml) overnight. IPTG was added to the medium to 0.1 mM and the culture was further incubated for 5 h.

Bacterial cells thus obtained were collected, disrupted with a Minibeatbeater 8 (BIOSPEC Inc.), and centrifuged to obtain the supernatant as the cell-free extract.

EXAMPLE 14

Reducing Activity of Acetoacetyl-CoA Reductase Derived from *Ralstonia eutropha*

The reducing activity of the cell-free extract obtained in Example 13 was assayed using ethyl 4-chloroacetoacetate and acetoacetyl-CoA as the substrate by the method according to Example 3. The results are shown in Table 3.

TABLE 3

| Substrate | AASCoA | ECAA | | S-ECHB | R-ECHB |
|---|---|---|---|---|---|
| Coenzyme | NADPH | NADPH | NADH | NADP$^+$ | NADP$^+$ |
| U/mg | 0.984 | 2.50 | 0.056 | 0 | 0 |
| Relative activity | 100% | 255% | 5.7% | 0% | 0% |

The cell-free extract expressing acetoacyl-CoA reductase showed the NADPH-dependent ethyl 4-chloroacetoacetate-reducing activity and its specific activity was 2.50 U/mg protein. In contrast, the HB101 strain containing no plasmid pSE-AER1 showed almost no ethyl 4-chloroacetoacetate-reducing activity.

The reducing activity with acetoacetyl-CoA was as low as about 39% of that with ethyl 4-chloroacetoacetate.

EXAMPLE 15

Oxidizing Activity of Acetoacetyl-CoA Reductase Derived from *Ralstonia eutropha*

The oxdizing activity of the cell-free extract obtained in Example 13 was assayed using ethyl (S)- or (R)-4-chloro-3-hydroxybutyrate as the substrate in the same manner as in Example 4. The results are shown in Table 3. The cell extract showed almost no oxidizing activity for either substrate.

EXAMPLE 16

Stereoselectivity of Acetoacetyl-CoA Reductase from *Ralstonia eutropha*

A reaction mixture (1 ml) containing 100 mM potassium phosphate buffer (pH 6.5), 1 mM NADP$^+$, 2% (122 mM) ethyl 4-chloroacetoacetate, acetoacyl-CoA reductase (1 U) prepared in Example 13, 243 mM glucose, and glucose dehyrogenase (2.8 U) (Wako Pure Chemical) was incubated at 25° C. overnight. Analysis was performed by the method according to Example 5, revealing a synthesis of ethyl 4-chloro-3-hydroxybutyrate with the optical purity of 99% ee (S) or more in a yield of 67%.

EXAMPLE 17

Construction of the Coexpression Plasmid pSE420D

The plasmid pSE420B constructed in Example 1 was digested with MunI and SpeI and ligated with the annealing product of the synthetic DNA SE420D-S (SEQ ID NO 13: AATTCTCGAGTAATCTAGAGGAATTCTAAAA) and the synthetic DNA SE420D-A (SEQ ID NO 14: CTAGTTTTAGAATTCCTCTAGATTACTCGAG) using T4 DNA ligase to obtain the plasmid pSE420D. The restriction map of pSE420D is shown in FIG. 1.

EXAMPLE 18

Cloning of Glucose Dehydrogenase Gene Derived from *Bacillus subtilis*

In order to regenerate the reduced nicotinamide adenine dinucleotide phosphate, the glucose dehydrogenase gene derived from *Bacillus subtilis* (J. Bateriol. 166, 238–243 (1986)) was cloned.

For the PCR cloning of only the open reading frame portion of the glucose dehydrogenase gene based on the nucleotide sequence described in the literature, the primers BSG-ATG1 (SEQ ID NO 15: GAGGAATTCATACATGTATCCAGATTTAAAAGGAA) and BSG-TAA2 (SEQ ID NO 16: GGTAAGCTTTCATTAACCGCGGCCTGCCTG) were synthesized based on the sequences at the 5'- and 3'-ends of the structural gene.

Using the chromosomal DNA of *Bacillus subtilis* prepared in Example 7 as the template and the BSG-ATG1 and BSG-TAA2 primers, 30 cycles of PCR (95° C. for 30 sec, 50° C. for 1 min, and 75° C. for 3 min and 15 sec) were performed, obtaining the amplified DNA fragments.

The thus-obtained DNA fragments were digested with EcoRI and HindIII and the digestion product was ligated with the plasmid vector pSE420L constructed in Example 17 digested with the same two restriction enzymes using T4 DNA ligase to obtain the plasmid pSE-BSG1.

Analysis of the nucleotide sequence of the DNA insert resulted in the perfect coincidence with that listed in the database (DDBJ Accession No. M12276).

The nucleotide sequence of the glucose dehydrogenase gene thus obtained is shown in SEQ ID NO: 17 and the amino acid sequence of the protein encoded by the gene in SEQ ID NO: 18.

EXAMPLE 19

Construction of the Plasmid pSG-ECR1 Coexpressing the β-Ketoacyl-ACP Reductase Gene Derived from *Escherichia coil* and the Glucose Dehydrogenase Gene Derived from *Bacillus subtilis*

The plasmid pSE-ECR1 constructed in Example 1 was digested with BamHI and XhoI to obtain the DNA fragment containing the β-ketoacyl-ACP reductase gene derived from *Escberichia coli*.

Figure 2:
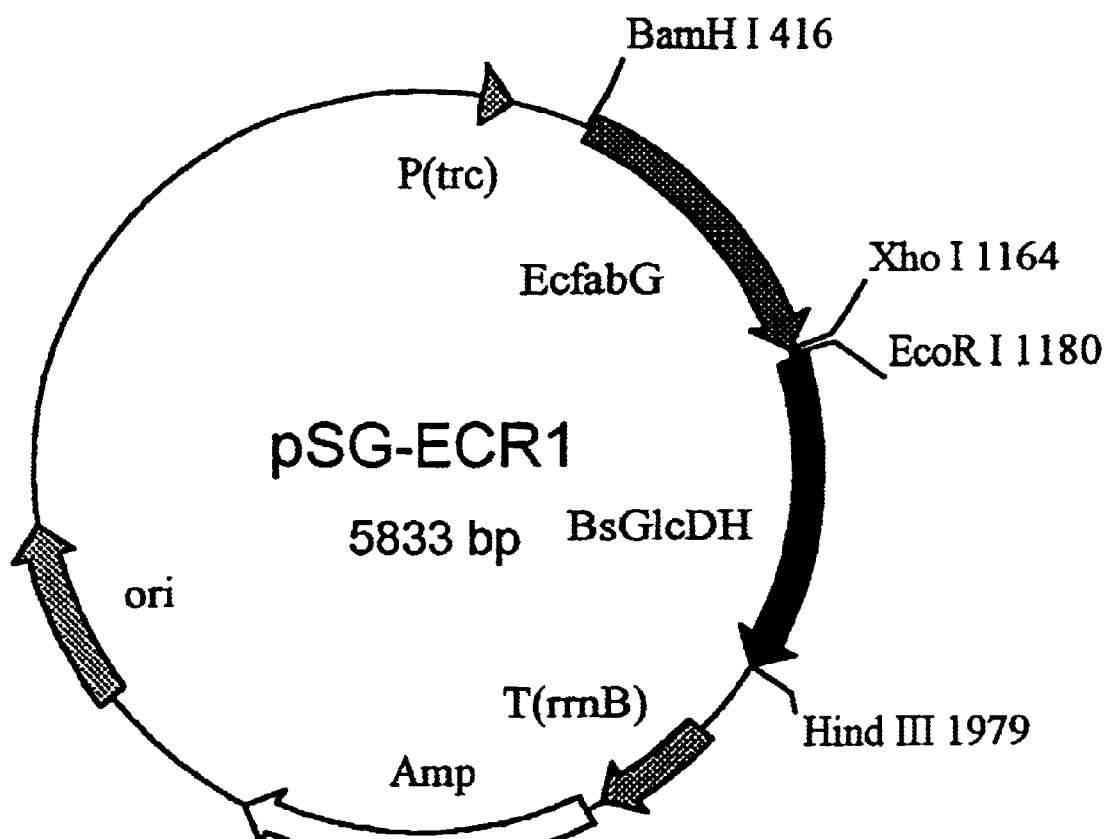
FIG. 2 shows the restriction map of plasmid pSG-ECR1. P(trc) represents the trc promoter, EcfabG the β-ketoacyl ACP reductase gene derived from Escherichia coli, BsG1cDH the glucose dehydrogenase gene derived from Bacillus subtilis, T(rrnB) the rrnB T1T2 terminator, Amp the β-lactamase gene for ampicillin resistance, and ori the replication origin of plasmid.

The plasmid pSE-BSG1 containing the glucose dehydrogenase gene derived from *Bacillus subtilis* constructed in Example 17 was digested with BamHI and XhoI, ligated to the above DNA fragment containing the β-ketoacyl-ACP reductase gene derived from *Escherichia coli* using T4 DNA ligase to obtain the plasmid pSE-ECR1 capable of coexpressing glucose dehydrogenase and β-ketoacyl-ACP reductase. The restriction map of the plasmid pSE-ECR1 is shown in FIG. 2.

EXAMPLE 20

Construction of the Plasmid pSG-ECR1 Coexpressing the β-Ketoacyl-ACP Reductase Gene Derived from *Bacillus subtilis* and the Glucose Dehydrogenase Gene Derived from *Bacillus subtilis*

The plasmid pSE-ECR1 constructed in Example 7 was digested with NcoI and XhoI to obtain the DNA fragment containing the β-ketoacyl-ACP reductase gene derived from *Bacillus subtilis*.

Figure 3:
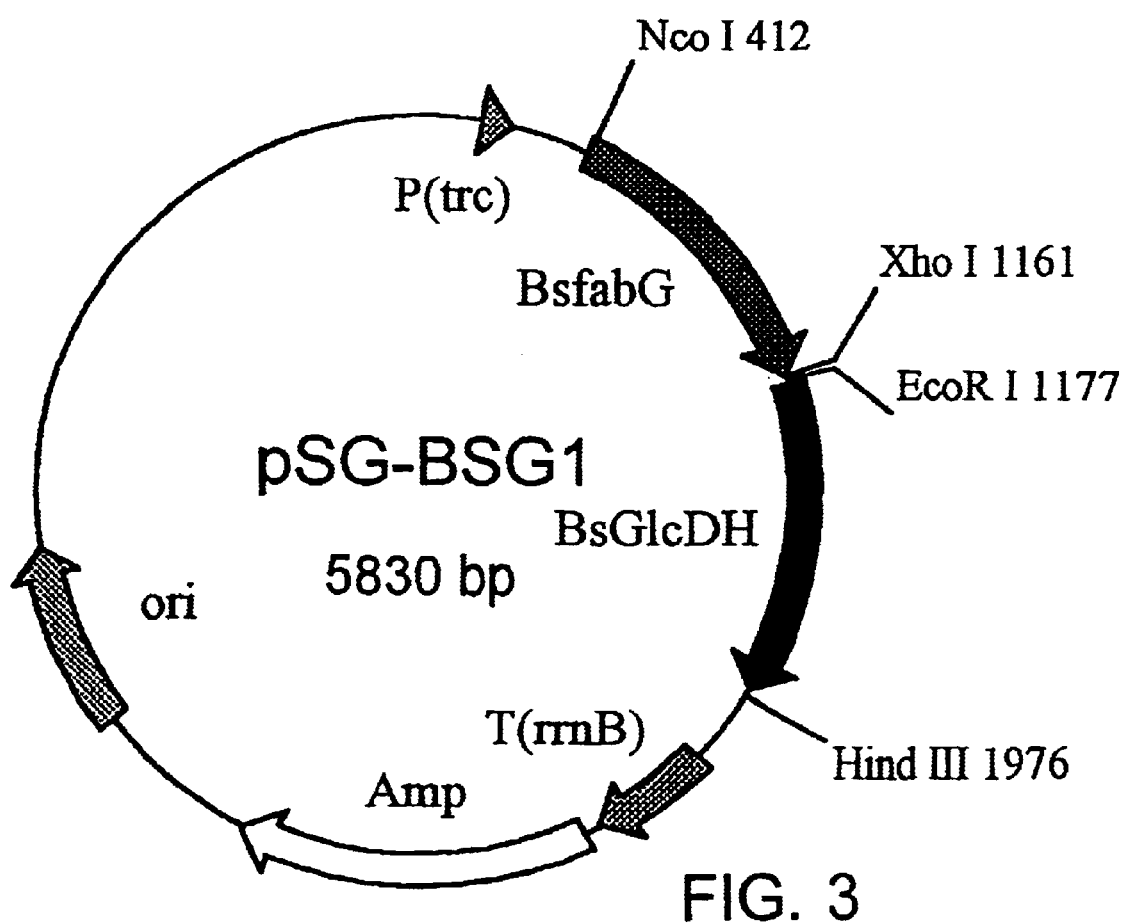
FIG. 3 shows the restriction map of plasmid pSG-BSR1. P(trc) represents the trc promoter, BcfabG the β-ketoacyl ACP reductase gene derived from Bacillus subtilis, BSG1cDH the glucose dehydrogenase gene derived from Bacillus subtilis, T(rrnB) the rrnB T1T2 terminator, Amp the β-lactamase gene for ampicillin resistance, and ori the replication origin of plasmid.

The plasmid pSE-BSG1 containing the glucose dehydrogenase gene derived from *Bacillus subtilis* constructed in Example 17 was digested with BamHI and XhoI, ligated to the above DNA fragment containing the β-ketoacyl-ACP reductase gene derived from *Bacillus subtilis* using T4 DNA ligase to obtain the plasmid pSG-BSR1 capable of coexpressing glucose dehydrogenase and β-ketoacyl-ACP reductase. The restriction map of the plasmid pSG-BSR1 is shown in FIG. 3.

EXAMPLE 21

Construction of Plasmid pSG-AER1 Coexpressing the Acetoacetyl-CoA Reductase Gene Derived from *Ralstonia eutropha* and the Glucose Dehydrogenase Gene Derived from *Bacillus subtilis*

The plasmid pSE-AER1 constructed in Example 12 was digested with BamHI and XhoI to obtain the DNA fragment containing the acetoacetyl-CoA reductase gene derived from *Ralstonia eutropha*.

Figure 4:
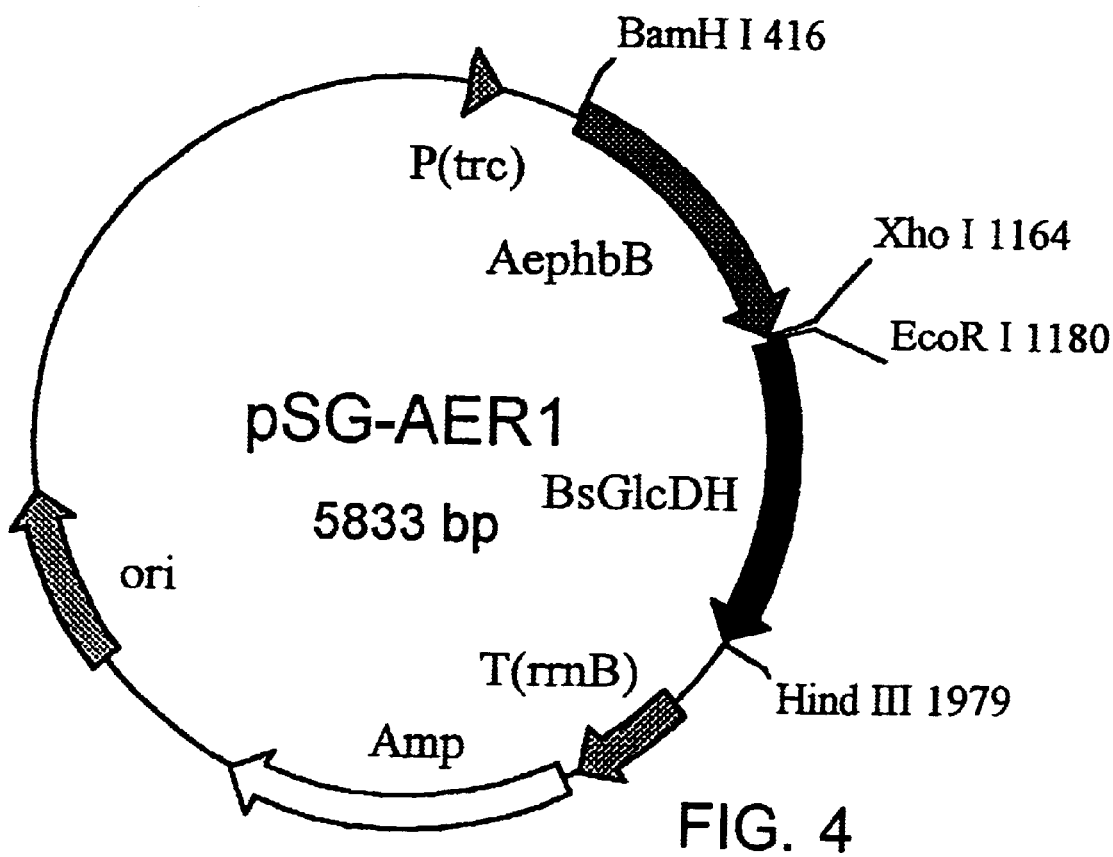
FIG. 4 shows the restriction map of plasmid pSG-AER1. P(trc) represents the trc promoter, AephbB the aetoacetyl-CoA reductase gene derived from Ralstonia eutropha, BsG1cDH the glucose dehydrogenase gene derived from Bacillus subtilis, T(rrnB) the rrnB T1T2 terminator, Amp the β-lactamase gene for ampicillin resistance, and ori the replication origin of plasmid.

The plasmid pSE-BSG1 containing the glucose dehydrogenase gene derived from *Bacillus subtilis* constructed in Example 17 was digested with NcoI and XhoI, ligated to the above DNA fragment containing the acetoacetyl-CoA reductase gene derived from *Ralstonia eutropha* using T4 DNA ligase to obtain the plasmid pSG-AER1 capable of coexpressing glucose dehydrogenase and acetoacetyl-CoA reductase. The restriction map of the plasmid pSG-AER1 is shown in FIG. 4.

EXAMPLE 22

Coexpression of Glucose Dehydrogenase Derived from *Bacillus subtilis* and β-ketoacyl-ACP Reductase Derived from *Escherichia coli* or β-Ketoacyl-ACP Reductase Derived from *Bacillus subtilis* or Acetoacetyl-CoA Reductase Derived from *Ralstonia eutropha*

*Escherichia coli* HB101 strain was transformed with the plasmids pSG-ECR1, PSG-BSR1, or pSG-AER1 to coexpress glucose dehydrogenase derived from *Bacillus subtilis* with β-ketoacyl-ACP reductase derived from *Escherichia coli* or with β-ketoacyl-ACP reductase derived from *Bacillus subtilis* or with acetoacetyl-CoA reductase derived from *Ralstonia eutropha*.

Recombinant *Escherichia coli* transformed with each plasmid was inoculated to the 2×YT medium (containing Bacto-Triptone 20 g, a Bacto-Yeast extract 10 g, and NaCl 10 g/l), cultured at 30° C. overnight. Adding 0.1 mM IPTG to the medium, the culturing was further performed for 4 h.

Three kinds of *Escherichia coli* transformants thus obtained were collected and subjected to the enzyme activity assay and the reducing reaction of ethyl 4-chloroacetoacetate.

EXAMPLE 23

Enzymatic Activity of *Escherichia coli* Cells Transformed with pSG-ECR1, pSG-BSR1 and pSG-AER1

*Escherichia coli* cells (corresponding to 2 ml of the culture) transformed with pSG-ECR1, pSG-BSR1, or pSG-AER1 prepared in Example 21 were separately suspended in 0.25 ml of a cell disrupting solution (containing 100 mM potassium phosphate buffer (pH 6.5), 0.02% 2-mercaptoethanol, and 0.5 M sodium chloride). The resulting solution was treated in a close ultrasonicator UCD-200TM (Cosmobio) for 3 min to disrupt the cells. The sonicated cell suspension was centrifuged and the supernatant was collected as the crude enzyme solution, which was subjected to the enzyme activity assay.

The ethyl 4-chloroacetoacetate-reducing activity was assayed in the same manner as in Example 3.

Glucose dehydrogenase activity was assayed in a reaction solution containing 100 mM potassium phosphate bufferr (pH 6.5), 2.5 mM NAD$^+$, 100 mM D-glucose, and the enzyme at 25° C.

One unit of each enzyme was defined as the amount of the enzyme catalyzing the formation of 1 μmol NADH per min under the above-described reaction conditions.

Each enzyme activity and SECHB productivity of the crude enzyme t solution obtained from recombinant *E. coli* containing pSG-ECR1, pSG-BSRI$_1$, or pSG-AER1 are shown in Table 4.

TABLE 4

| Plasmid | Enzyme activity (U/ml-br) | | SECHB synthesis | |
|---|---|---|---|---|
| | GlcDH | ECAA-R | (g/l) | ee (%) S |
| pSG-ECR1 | 0.476 | 0.151 | 20.3 | 93.7 |
| pSG-BSR1 | 4.089 | 0.203 | 42.3 | 98.0 |
| pSG-AER1 | 3.717 | 1.475 | 42.8 | 99.3 |

U/ml-br: enzyme activity per ml of the culture
GlcDH: glucose dehydrogenase
ECAA-R: ethyl 4-chloroacetoacetate reductase
SECHB: ethyl (S)-4-chloro-3-hydroxybutyrate

*E. coli* cells with no plasmid have neither glucose dehydrogenase activity nor ethyl 4-chloroacetoacetate reductase activity, while recombinant *E. coli* cells with pSG-ECR1, pSG-BSR1, or pSG-AER1 showed both enzymatic activities, indicating expression of the two enzyme genes introduced in the plasmids.

EXAMPLE 24

Synthesis of Ethyl (S)-4-chloro-3-hydroxybutyrate Using *Escherichia coli* Transformed with pSG-ECR1, pSG-BSR1, or pSG-AER1

Ethyl 4-chloroacetoacetate was reduced using *Escherichia coli* containing pSG-ECR1, pSG-BSR1, or pSG-AER1 prepared in Example 21.

A reaction solution (20 ml) containing each *Escherichia coli* cell prepared from 20 ml of the culture, 200 mM potassium phosphate buffer (pH 6.5), 4% ethyl 4-chloroacetoacetate, 486 mM D-glucose, and 1 mM NADP$^+$ was incubated at 25° C. under stirring overnight.

The amount and the optical purity of ethyl (S)-4-chloro-3-hydroxybutyrate were determined in the same manner as in Example 5. The results are shown in Table 4. As shown in Table 4, all of the three kinds of the *E. coli* transformants could produce (S)-4-chloro-3-hydroxybutyrate efficiently with high sterepselectivity.

What is claimed is:

1. A method for producing a (S)-4-halo-3-hydroxybutyric acid ester, the method comprising asymmetrically reducing a 4-haloacetoacetic acid ester or its derivative with a purified acetoacetyl-CoA reductase (EC 1.1.1.36) that participates in a poly-β-hydroxy fatty acid biosynthesis system.

2. The method of claim 1, wherein said acetoacetyl-CoA reductase is from a microorganism belonging to the genus *Ralstonia*.

3. The method of claim 2, wherein the microorganism is *Ralstonia eutropha*.

4. The method of claim 1, wherein said acetoacetyl-CoA reductase comprises the amino acid sequence of SEQ ID NO:9.

5. The method of claim 1, wherein said 4-haloacetoacetic acid ester is 4-chloroacetoacetic acid ester.

6. The method of claim 1, wherein said 4-haloacetoacetic acid ester is ethyl 4-chloroacetoacetate.

7. The method of claim 1, wherein said acetoacetyl-CoA reductase is from *Zoogloe ramigera*.

8. The method of claim 1, wherein the reduction is carried out in the presence of glucose dehydrogenase.

9. The method of claim 2, wherein the reduction is carried out in the presence of glucose dehydrogenase.

10. The method of claim 3, wherein the reduction is carried out in the presence of glucose dehydrogenase.

11. The method of claim 4, wherein the reduction is carried out in the presence of glucose dehydrogenase.

12. The method of claim 5, wherein the reduction is carried out in the presence of glucose dehydrogenase.

13. The method of claim 6, wherein the reduction is carried out in the presence of glucose dehydrogenase.

14. The method of claim 7, wherein the reduction is carried out in the presence of glucose dehydrogenase.

15. The method of claim 2, wherein the 4-haloacetoacetic acid ester is 4-chloroacetoacetic acid ester.

16. The method of claim 2, wherein the 4-haloacetoacetic acid ester is ethyl 4-chloroacetoacetate.

17. The method of claim 3, wherein the 4-haloacetoacetic acid ester is 4-chloroacetoacetic acid ester.

18. The method of claim 3, wherein the 4-haloacetoacetic acid ester is ethyl 4-chloroacetoacetate.

19. The method of claim 4, wherein the 4-haloacetoacetic acid ester is 4-chloroacetoacetic acid ester.

20. The method of claim 4, wherein the 4-haloacetoacetic acid ester is ethyl 4-chloroacetoacetate.

21. The method of claim 7, wherein the 4-haloacetoacetic acid ester is 4-chloroacetoacetic acid ester.

22. The method of claim 7, wherein the 4-haloacetoacetic acid ester is ethyl 4-chloroacetoacetate.

* * * * *

UNITED STATES PATENT AND TRADEMARK OFFICE
CERTIFICATE OF CORRECTION

PATENT NO. : 6,855,525 B1
DATED : February 15, 2005
INVENTOR(S) : Hiroaki Yamamoto It is certified that error appears in the above-identified patent and that said Letters Patent is hereby corrected as shown below:

Title page,
Item [57], ABSTRACT,
Line 14, delete "of ethyl, 4-chloroacetoacetate" and replace with -- of ethyl 4-chloroacetoacetate --.

Column 37,
Line 46, delete "from *Zoogloe ramigera*" and replace with -- from *Zoogloea ramigera* --.

Signed and Sealed this

Third Day of January, 2006

JON W. DUDAS
*Director of the United States Patent and Trademark Office*